(12) United States Patent
Ishii et al.

(10) Patent No.: US 9,145,547 B2
(45) Date of Patent: Sep. 29, 2015

(54) NUCLEAR REPROGRAMMED CELLS GENERATED BY INTRODUCTION OF A HISTONE H2AA OR TH2A GENE, A HISTONE H2BA OR TH2B GENE, OR A PHOSPHORYLATION-MIMIC OF HISTONE CHAPERON NPM2 GENE, AN OCT FAMILY GENE AND A KLF FAMILY GENE INTO A MAMMALIAN SOMATIC CELL

(75) Inventors: Shunsuke Ishii, Wako (JP); Toshie Shinagawa, Wako (JP)

(73) Assignee: RIKEN, Wako-shi, Saitama (JP)

( * ) Notice: Subject to any disclaimer, the term of this patent is extended or adjusted under 35 U.S.C. 154(b) by 321 days.

(21) Appl. No.: 13/597,854

(22) Filed: Aug. 29, 2012

(65) Prior Publication Data
US 2013/0052643 A1 Feb. 28, 2013

Related U.S. Application Data

(60) Provisional application No. 61/528,989, filed on Aug. 30, 2011.

(51) Int. Cl.
*C12N 5/074* (2010.01)
*G01N 33/50* (2006.01)

(52) U.S. Cl.
CPC .......... *C12N 5/0696* (2013.01); *G01N 33/5073* (2013.01); *C12N 2501/065* (2013.01); *C12N 2501/603* (2013.01); *C12N 2501/604* (2013.01); *C12N 2501/998* (2013.01); *C12N 2510/00* (2013.01)

(58) Field of Classification Search
CPC .......... G01N 33/6896; G01N 33/5073; C12N 2501/603; C12N 2501/604; C12N 2501/998; C12N 2510/00; C12N 5/0696; C12N 2501/065; G06F 19/18; G06F 19/20; G06F 19/24
See application file for complete search history.

(56) References Cited

U.S. PATENT DOCUMENTS

| 2009/0047263 | A1 | 2/2009 | Yamanaka et al. |
| 2009/0068742 | A1 | 3/2009 | Yamanaka |
| 2009/0227032 | A1 | 9/2009 | Yamanaka et al. |
| 2010/0062533 | A1 | 3/2010 | Yamanaka |
| 2010/0210014 | A1 | 8/2010 | Yamanaka |
| 2010/0216236 | A1 | 8/2010 | Yamanaka |

FOREIGN PATENT DOCUMENTS

| JP | 2010110289 A | 5/2010 |
| JP | 2010252786 A | 11/2010 |
| WO | WO-2007069666 A1 | 6/2007 |

OTHER PUBLICATIONS

Miyamoto et al. Reprogramming Events of Mammalian Somatic Cells Induced by *Xenopus laevis* Egg Extracts. Molec. Reprod. Devel., 2007, vol. 74, pp. 1268-1277.*
Stadtfeld et al. Induced pluripotent stem cells generated without viral integration. Science, vol. 322. pp. 945-949.*
Yu et al. Human Induced Pluripotent Stem Cells Free of Vector and Transgene Sequences. Science, 2009, vol. 324, pp. 797-802.*
Pearson et al. An Introduction to Sequence Similarity ("Homology") Searching. Curr Protoc Bioinformatics. Jun. 2013; doi:10.1002/0471250953.bi0301s42.*
Han et al., "Tbx3 Improves the germ-line competency of induced pluripotent stem cells" *Nature*, vol. 463, Feb. 25, 2010.
Zhao et al., "Two Supporting Factors Greatly Improve the Efficiency of Human iPSC Generation", *Cell Stem Cell* 3, Nov. 6, 2008, pp. 475-479.
Tsubooka et al., "Roles of Sall4 in the generation of pluripotent stem cells from blastocysts and fibroblasts", *Genes to Cells* (2009) 14, 683-694.
Heng et al., "The Nuclear Receptor Nr5a2 Can Replace Oct4 in the Reprogramming of Murine Somatic Cells to Pluripotent Cells", *Cell Stem Cell* 6, 167-174, Feb. 5, 2010.
Edel et al., "Rem2 GTPase maintains survival of human embryonic stem cells as well as enhancing reprogramming by regulating p53 and cyclin D1". *Genes Dev.* 2010 24:561-573.
Picanco-Castro et al., "Pluripotent Reprogramming of Fibroblasts by Lentiviralmediated Insertion of SOX2, C-MYC, and TCL-1A", *Stem Cells and Development*, vol. 20, No. 1, 2011, pp. 169-180.
Nagamatsu et al., "A Germ Cell-specific Gene, Prmt5, Works in Somatic Cell Reprogramming", *Journal of Biological Chemistry* pp. 10641-10648, vol. 286, No. 12, Mar. 25, 2011.
Maekawa et al., "Direct reprogramming of somatic cells is promoted by maternal transcription factor Glis1", *Nature* pp. 225-229, Jun. 9, 2011, vol. 474.
Judson et al., "Embryonic stem cell-specific microRNAs promote induced pluripotency", *Nature Biotechnology*, pp. 459-461, vol. 27, No. 5, May 2009.
Li et al., "Small RNA-mediated regulation of iPS cell generation", *The EMBO Journal*, pp. 823-834, vol. 30, No. 5, 2011.
Kamata et al., "Live Cell Monitoring of hiPSC Generation and Differentiation Using Differential Expression of Endogenous microRNAs", *PLoS One*, pp. 1-12, Jul. 2010, vol. 5, Issue 7.
Lin et al., "Regulation of somatic cell reprogramming through inducible mir-302 expression", *Nucleic Acids Research*, pp. 1054-1065, 2011, vol. 39, No. 3.
Miyoshi et al., "Reprogramming of Mouse and Human Cells to Pluripotency Using Mature MicroRNAs", *Cell Stem Cell* 8, pp. 633-638, Jun. 3, 2011.
Shi et al., "A Combined Chemical and Genetic Approach for the Generation of Induced Pluripotent Stem Cells", pp. 525-528, *Cell Stem Cell* 2, Jun. 2008.
Huangfu et al., "Induction of pluripotent stem cells by defined factors is greatly improved by small-molecule compounds", *Nature Biotechnology*, pp. 795-797, vol. 26, No. 7, Jul. 2008.
Huangfu et al., "Induction of pluripotent stem cells from primary human fibroblasts with only *Oct4* and *Sox2*", *Nature Biotechnology*, pp. 1269-1275, vol. 26, No. 11, Nov. 2008.

(Continued)

*Primary Examiner* — Deborah Crouch
(74) *Attorney, Agent, or Firm* — Locke Lord LLP

(57) ABSTRACT

A method for generating a nuclear reprogrammed cell in accordance with the present invention includes the step of: introducing, into a somatic cell, (i) at least one gene selected from the group consisting of a gene encoding histone H2aa or a homologue thereof, a gene encoding histone H2ba or a homologue thereof, and a gene encoding a phosphorylation-mimic form of histone chaperon Npm2 or a phosphorylation-mimic form of a homologue of Npm2, and (ii) a nuclear reprogramming factor.

13 Claims, 6 Drawing Sheets
(6 of 6 Drawing Sheet(s) Filed in Color)

(56) References Cited

OTHER PUBLICATIONS

Mali et al., "Butyrate Greatly Enhances Derivation of Human Induced Pluripotent Stem Cells by Promoting Epigenetic Remodeling and the Expression of Pluripotency-Associated Genes", *Stem Cells* 2010; 28:713-720.
Liang et al., "Butyrate Promotes Induced Pluripotent Stem Cell Generation", *Journal of Biological Chemistry*, pp. 25516-25521, vol. 285, No. 33, Aug. 13, 2010.
Zhu et al., "Reprogramming of Human Primary Somatic Cells by OCT4 and Chemical Compounds", *Cell Stem Cell* 7, pp. 651-655, Dec. 3, 2010.
Marson et al., "Wnt Signaling Promotes Reprogramming of Somatic Cells to Pluripotency", *Cell Stem Cell* 3, pp. 132-135, Aug. 7, 2008.
Li et al., "Generation of Human-Induced Pluripotent Stem Cells in the Absence of Exogenous *Sox2*", *Stem Cells* 2009; 27:2992-3000.
Theunissen, et al., "Nanog Overcomes Reprogramming Barriers and Induces Pluripotency in Minimal Conditions", *Current Biology* 21, pp. 65-71, Jan. 11, 2011.
Xu et al., "Revealing a core signaling regulatory mechanism for pluripotent stem cell survival and self-renewal by small molecules", *PNAS*, pp. 8129-8134, May 4, 2010, vol. 107, No. 18.
Hanna et al. "Direct cell reprogramming is a stochastic process amenable to acceleration", *Nature*, pp. 595-601, vol. 462, Dec. 3, 2009.
Guo et al., "Klf4 reverts developmentally programmed restriction of ground state pluripotency", *Development* 136, pp. 1063-1069, (2009).
Lyssiotis, et al. "Reprogramming of murine fibroblasts to induced pluripotent stem cells with chemical complementation of Klf4", *PNAS*, pp. 8912-8917, Jun. 2, 2009, vol. 106, No. 22.
Li et al., "Pluripotency can be rapidly and efficiently induced in human amniotic fluid-derived cells", *Human Molecular Genetics*, pp. 4340-4349, 2009. vol. 18. No. 22.
Takenaka et al., "Effective generation of iPS cells from CD34+ cord blood cells by inhibition of p53", *Experimental Hematology* 2010;38:154-162.
Maherali et al., "Tgfβ Signal Inhibition Cooperates in the Induction of iPSCs and Replaces Sox2 and cMyc", *Current Biology* 19, pp. 1718-1723, Nov. 3, 2009.
Ichida et al., "A Small-Molecule Inhibitor of Tgf-β Signaling Replaces Sox2 in Reprogramming by Inducing *Nanog*", *Cell Stem Cell* 5, pp. 491-503, Nov. 6, 2009.
Chen et al., "E-Cadherin-Mediated Cell-Cell Contact Is Critical for Induced Pluripotent Stem Cell Generation", *Stem Cells* 2010;28:1315-1325.
Zhang et al., "PRC2 Complexes with JARID2, MTF2, and esPRC2p48 in ES Cells to Modulate ES Cell Pluripotency and Somatic Cell Reprogramming", *Stem Cells* 2011:29:229-240.
Li et al., "Apoptotic Caspases Regulate Induction of iPSCs from Human Fibroblasts", *Cell Stem Cell* 7, pp. 508-520, Oct. 8, 2010.
Kim et al., "Oct4-Induced Pluripotency in Adult Neural Stem Cells", *Cell* 136, pp. 411-419, Feb. 6, 2009.
Kim et al., "Direct reprogramming of human neural stem cells by OCT4", *Nature*, vol. 461, pp. 649-653, Oct. 1, 2009.
Zhou et al., "Generation of Induced Pluripotent Stem Cells Using Recombinant Proteins", *Cell Stem Cell* 4, pp. 381-384, May 8, 2009.
Kim et al., Generation of Human Induced Pluripotent Stem Cells by Direct Delivery of Reprogramming Proteins, *Cell Stem Cell* 4, pp. 472-476, Jun. 5, 2009.
Takahashi et al., "Induction of Pluripotent Stem Cells from Mouse Embryonic and Adult Fibroblast Cultures by Defined Factors", *Cell* 126, pp. 663-676, Aug. 25, 2006.
Okita et al., "Generation of germline-competent induced pluripotent stem cells", *Nature*, pp. 313-317, vol. 448, Jul. 19, 2007.
Feng et al., "Reprogramming of fibroblasts into induced pluripotent stem cells with orphan nuclear receptor Esrrb", *Nature Cell Biology*, pp. 197-203, vol. 11, No. 2, Feb. 2009.
Feng et al., "Molecules that Promote or Enhance Reprogramming of Somatic Cells to Induced Pluripotent Stem Cells", *Cell Stem Cell* 4, pp. 301-312, Apr. 3, 2009.
Wakayama et al., "Full-term development of mice from enucleated oocytes injected with cumulus cell nuclei", *Nature*, pp. 369-374, Jul. 23, 1998.
Mikkelsen et al., "Genome-wide maps of chromatin state in pluripotent and lineage-committed cells", *Nature*, pp. 553-560, vol. 448, Aug. 2, 2007.
Meissner, "Epigenetic modifications in pluripotent and differentiated cells", *Nature Biotechnology*, pp. 1079-1088, vol. 28, No. 10, Oct. 2010.
Marzluff et al., "The Human and Mouse Replication-Dependent Histone Genes", *Genomics*, pp. 487-498, vol. 80, No. 5, Nov. 2002.
Trostle-Weige et al., "Isolation and Characterization of TH2A, a Germ Cell-specific Variant of Histone 2A in Rat Testis", *The Journal of Biological Chemistry*, pp. 5560-5567, vol. 257, No. 10, Issue of May 25, 1982.
Brock et al., "Meiotic synthesis of testis histones in the rat", *Proc. Natl. Acad. Sci. USA*, pp. 371-375, vol. 77, No. 1, Jan. 1980.
Avvakumov et al., "Histone Chaperones: Modulators of Chromatin Marks", *Molecular Cell* 41, pp. 502-514, Mar. 4, 2011.
Bürglin, et al., "Cloning of nucleoplasmin from *Xenopus laevis* oocytes and analysis of its development expression", *Genes and Development* 1:97-107 (1987).
Tamada et al., "Chromatin Decondensation and Nuclear Reprogramming by Nucleoplasmin", *Molecular and Cellular Biology*, vol. 26, No. 4, pp. 1259-1271, Feb. 2006.
Bañuelos et al., "Phosphorylation of Both Nucleoplasmin Domains is Required for Activation of Its Chromatin Decondensation Activity", *The Journal of Biological Chemistry*, pp. 21213-21221, vol. 282, No. 29, Jul. 20, 2007.
Nakagawa et al., "Generation of induced pluripotent stem cells without Myc from mouse and human fibroblasts", *Nature Biotechnology*, pp. 101-106. vol. 26, No. 1, Jan. 2008.
Okabe et al., "'Green Mice' as a source of ubiquitious green cells", *FEBS Letters*, pp. 313-319, 407 (1997).
Huang, "KinasePhos: a web tool for identifying protein kinase-specific phosphorylation sites", *Nucleic Acids Research*, 2005, pp. W226-W229, vol. 33, Web Server issue.

* cited by examiner

FIG. 1

```
Histone H2A
              1          10         20         30         40         50         60         70
Canonical H2ao  SGRGKQGGKA RAKAKTRSSR AGLQFPVGRV HRLLRKGNTS ERVGAGAPVY LAAVLEYLTA EILELAGNAA
         H2a8  SGPTKMGGKA RAKVKSRSSR AGLQFPVGRV HRLLRKQGNYA QRIGAGAPVY LAAVLEYLIA EVLELAGNAA
              71         80         90         100        110        120
         H2ao  RDNKKTRIIP RHLQLAIRND EELNKLLGRV TIAQGGVLPN IQAVLLPKKT ESHHKAKGK
         H2a8  RDNKKTRITP RHLQLAIRND EELNKLLGRV TIAQGGVLPN IQAVLLPKKT ESH-KSQTK Histone H2B
              1          10         20         30         40         50         60         70
Canonical H2bf  PEP-AKSAPA PKKGSKKAVT KAQKKDGKKR KRSRKESYSV YVYKVLKQVH PDTGISSKAM GIMNSFVNDI
         H2ba  PEVAVKGATI SKKGFKKAVT KTQKKEGKKR KRCRKESYSI YIYKVLKQVH PDTGISSKAM SIMNSFVTDI
              71         80         90         100        110        120
         H2bf  FERIASEASR LAHYNKRSTI TSRETQTAVR LLLPGELAKH AVSEGTKAVT KYTSSK
         H2ba  FERIASEASR LAHYNKRSTI TSREIQTAVR LLLPGELAKH AVSEGTKAVT KYTSSK
```

NUCLEAR REPROGRAMMED CELLS GENERATED BY INTRODUCTION OF A HISTONE H2AA OR TH2A GENE, A HISTONE H2BA OR TH2B GENE, OR A PHOSPHORYLATION-MIMIC OF HISTONE CHAPERON NPM2 GENE, AN OCT FAMILY GENE AND A KLF FAMILY GENE INTO A MAMMALIAN SOMATIC CELL

CROSS-REFERENCE TO RELATED APPLICATION

This Nonprovisional application claims priority under 35 U.S.C. §119 on Provisional Patent Application No. 61/528,989 filed in USPTO on Aug. 30, 2011, the entire contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Aug. 28, 2012, is named 89230_70904_SequenceListing_ST25.txt and is 5,127 bytes in size.

TECHNICAL FIELD

The present invention relates to a new method for generating a nuclear reprogrammed cell, and a use thereof.

BACKGROUND ART

Research on generation of a so-called iPS cell (induced pluripotent stem cell) and a use of the iPS cell has been actively carried out so as to apply the iPS cell to regenerative medicine, for example (see Patent Literature 1).

The iPS cell is generated by causing a given nuclear reprogramming factor to act on a somatic cell. Therefore, the iPS cell is less likely to cause an ethical problem as compared to an embryonic stem cell (ES cell) established from an early embryo.

CITATION LIST

Patent Literature

Patent Literature 1
International Publication No. WO2007/69666 (Publication Date: Jun. 21, 2007)

SUMMARY OF INVENTION

Technical Problem

Various reports have been made on a method for generating a nuclear reprogrammed cell. For example, according to a method described in Patent Literature 1 for generating an iPS cell, a nuclear reprogramming factor, for example is screened based on knowledge acquired from ES cell expression profiling. Namely, this is an approach in which a factor specifically expressed in an ES cell is used as a nuclear reprogramming factor for iPS cell generation.

Alternatively, the method for generating a nuclear reprogrammed cell is exemplified by another approach in which a factor specifically expressed in an oocyte is used in conformity with generation of a somatic cell clone. However, no report has been substantially made that a nuclear reprogrammed cell can be generated by introducing, into a somatic cell, a factor selected in accordance with the another approach. Successful generation of a nuclear reprogrammed cell in accordance with a new approach allows a rapid acceleration in research on and application of regenerative medicine, for example.

The present invention has been made in view of the problems, and an object of the present invention is to provide a new method for generating a nuclear reprogrammed cell by use of a factor specifically expressed in an oocyte, and a use thereof.

Solution to Problem

In order to attain the object, the present invention encompasses the following:

(1) A method for generating a nuclear reprogrammed cell from a somatic cell, the method including the step of: introducing, into the somatic cell, (i) at least one gene selected from the group consisting of a gene encoding histone H2aa or a homologue thereof, a gene encoding histone H2ba or a homologue thereof, and a gene encoding a phosphorylation-mimic form of histone chaperon Npm2 or a phosphorylation-mimic form of a homologue of Npm2, and (ii) a nuclear reprogramming factor.

(2) A nuclear reprogrammed cell generated by a method mentioned in the above (1).

(3) A somatic cell generated by differentiation of a nuclear reprogrammed cell mentioned in the above (2).

(4) A method for screening a nuclear reprogramming factor, the method including the steps of: a) preparing a somatic cell into which at least one gene selected from the group consisting of a gene encoding histone H2aa or a homologue thereof, a gene encoding histone H2ba or a homologue thereof, and a gene encoding a phosphorylation-mimic form of histone chaperon Npm2 or a phosphorylation-mimic form of a homologue of Npm2 is introduced so as to be expressed; b) introducing a candidate for the nuclear reprogramming factor into a somatic cell or bringing the candidate for the nuclear reprogramming factor into contact with the somatic cell; and c) determining whether or not the somatic cell has been nuclear reprogrammed after the steps a) and b) have been carried out, the somatic cell in the step a) and the somatic cell in the step b) being identical.

(5) An inducer from a somatic cell to a nuclear reprogrammed cell, including: at least one gene selected from the group consisting of a gene encoding histone H2aa or a homologue thereof, a gene encoding histone H2ba or a homologue thereof, and a gene encoding a phosphorylation-mimic form of histone chaperon Npm2 or a phosphorylation-mimic form of a homologue of Npm2; and a gene encoding a nuclear reprogramming factor.

(6) A somatic cell into which all the gene encoding histone H2aa or a homologue thereof, the gene encoding histone H2ba or a homologue thereof, and the gene encoding a phosphorylation-mimic form of histone chaperon Npm2 or a phosphorylation-mimic form of a homologue of Npm2 are introduced so as to be expressed.

Advantageous Effects of Invention

The present invention yields an effect of providing a new method for generating a nuclear reprogrammed cell, and a use thereof.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1 shows amino acid sequences of mouse-derived histone variants (histone H2aa and histone H2ba) used in Examples of the present invention. Amino acid sequences of two mouse histone variants, H2aa (Accession no. AAO06231) and H2ba (Accession no. CAA62299) are shown together with those of mouse canonical somatic cell histones, H2A (H2ao, Accession no. AAO06223) and H2B (H2bf, Accession no. AAO06245). H2aa and H2bb have the 15- and 16-amino acid differences (red) compared to the canonical histones.

Scatter plots comparing GFP intensity to autofluorescence are shown (b). Mean values of four independent experiments±SEM are indicated (c).

Figure 3:
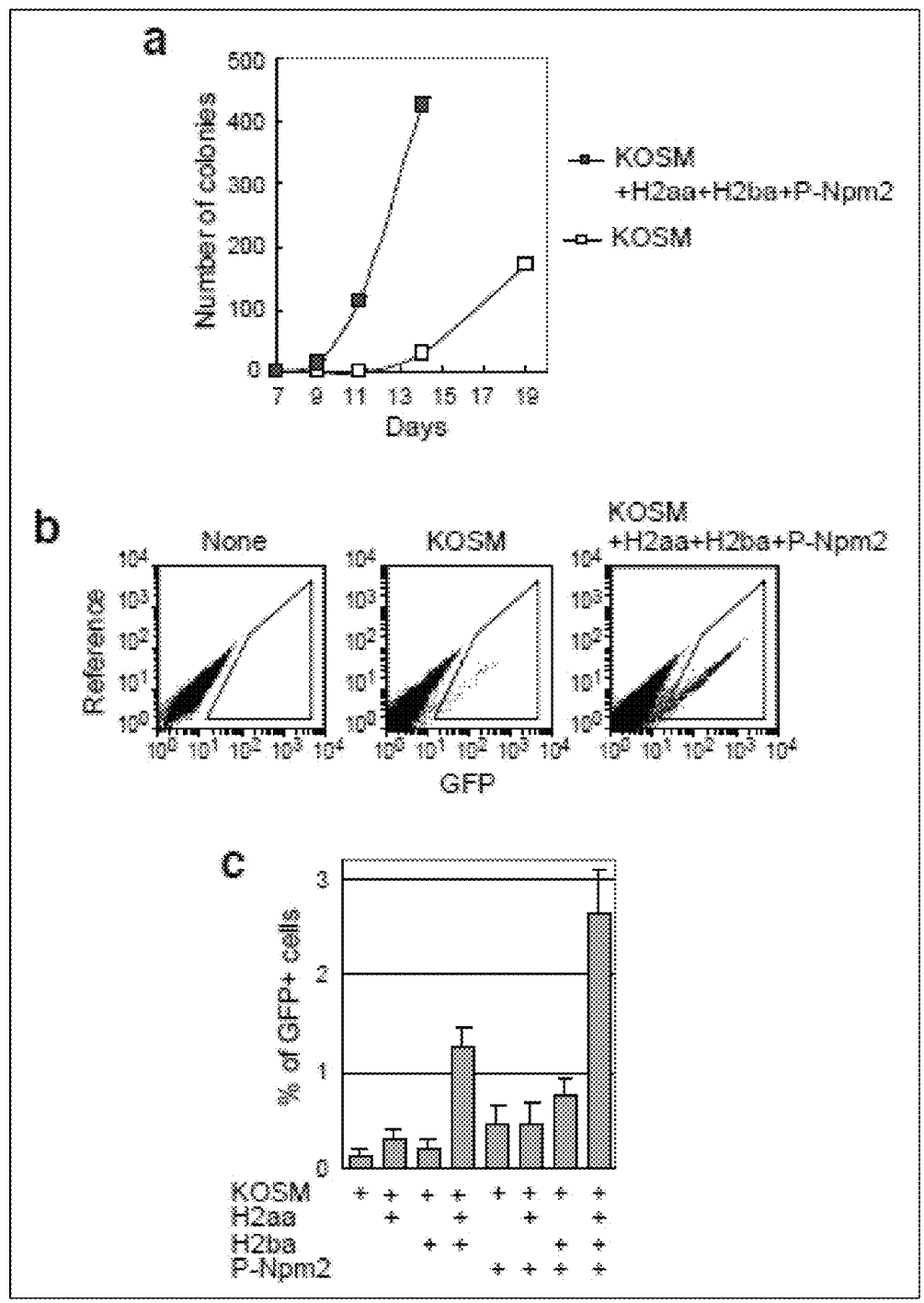
FIG. 3, which shows results of the Examples of the present invention, shows that histone H2aa, histone H2ba, and a phosphorylation-mimic form of histone chaperon Npm2 promote nuclear reprogramming of a somatic cell. a), Acceleration of iPSCs generation by Yamanaka four factors (KOSM:Klf-4, Oct3/4, Sox-2, and c-Myc) by two histone variants. MEFs from Nanog-GFP expressing mice were infected with the viruses expression Yamanaka four factors (KOSM) or with the viruses expressing Yamanaka four factors and H2aa, H2ba, and the phosphorylation-mimic form of nucleoplasmin (P-Npm2). The number of GFP+ colonies at various times after infection are shown. Data represent mean±SEM of three independent experiments (n=3). b) and c), Two histone variants and P-Npm2 stimulated iPSC generation by Yamanaka four factors. MEFs from the Nanog-GFP mice were infected with the retroviruses to express indicated protein, and the number of the GFPpositive cells was analyzed using FACS analysis 10 days after virus transduction.
Figure 4:
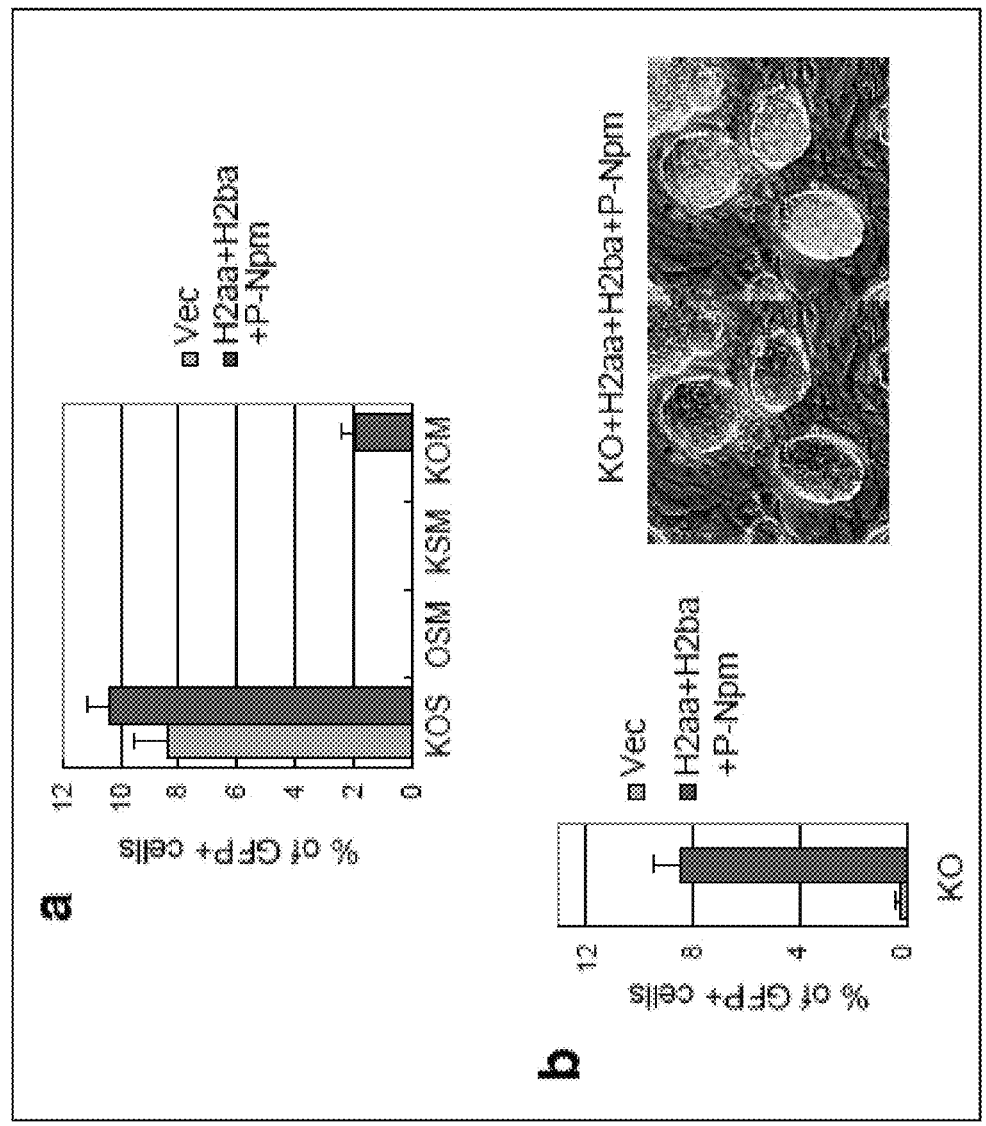

FIG. 4, which shows results of the Examples of the present invention, shows a result of consideration of a combination of histone H2aa, histone H2ba, and a phosphorylation-mimic form of histone chaperon Npm2 with a nuclear reprogramming factor. a), Different combinations of three factors among Yamanaka four factors with H2aa/H2ba/P-Npm2. The efficiency of iPSCs generation was measured as described in c) of FIG. 3 18 days after infection with the viruses to express the indicated three factors among Yamanaka four factors with or without the viruses to express H2aa, H2ba, and P-Npm2. Data represent mean±SEM of three independent retrovirus transduction experiments. b), Nanog-GFP MEFS were infected with the viruses to express Klf-4 and Oct3/4 with or without the viruses expressing H2aa/H2ba/P-Npm2. The GFP+ iPSCs were measured using FACS 25 days after infection as described above. Data represent mean±SEM of three independent retrovirus transduction experiments. Morphology of the generated iPS cells at passage 1 is shown on the right.

Figure 5:
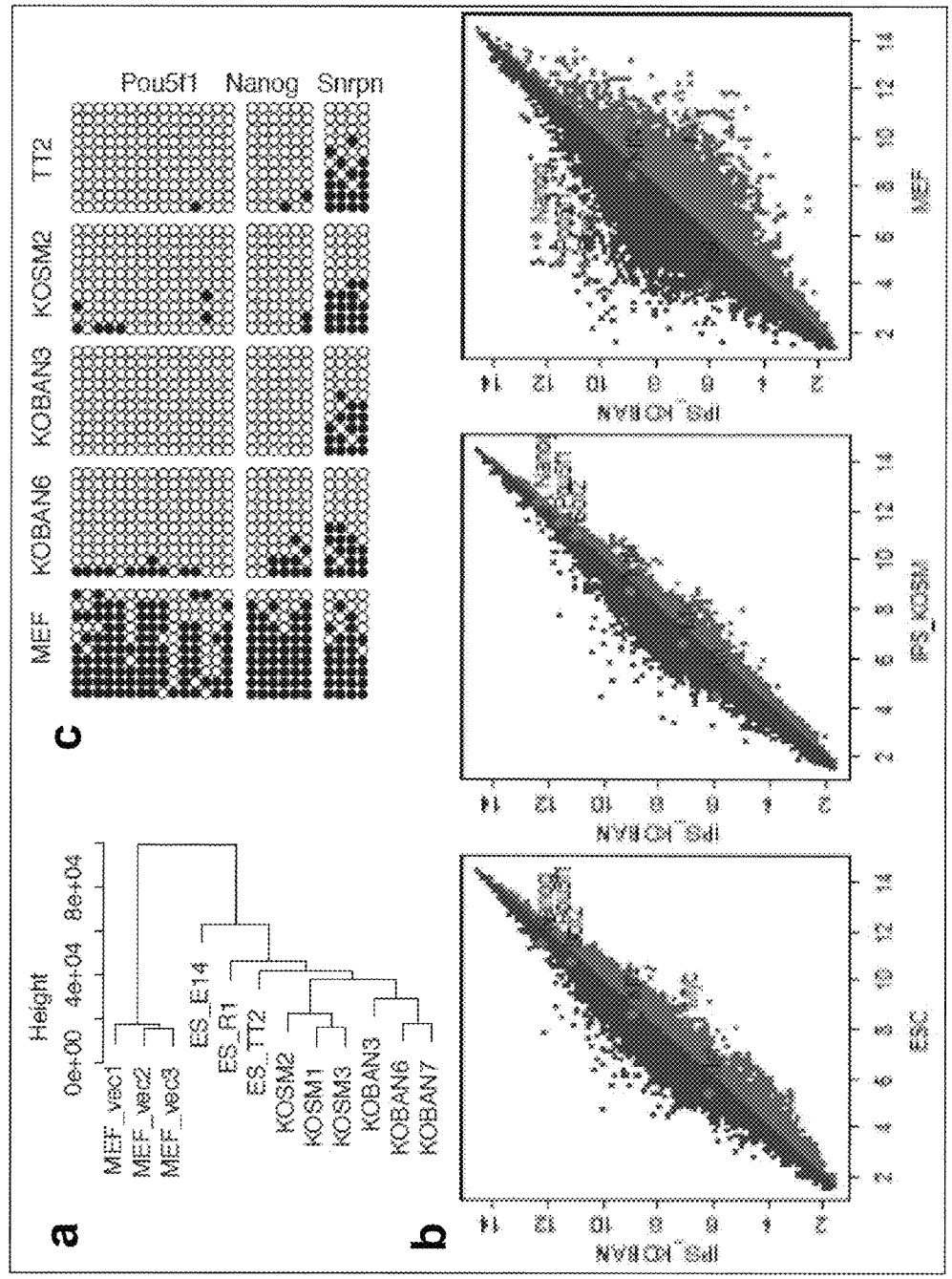

FIG. 5 shows a gene expression profile and a DNA methylation status of nuclear reprogrammed cells obtained in the Examples of the present invention. a), Unsupervised clustering based on microarray expression data. The dendrogram was generated by complete linkage hierarchical clustering using Pearson correlation on all measured genes. Three ES cell lines (TT2, R1, and E14), three clones of iPS cells generated by Yamanaka four factors (KOSM), three clones of iPS cells generated by Klf-4, Oct3/4, H2ba, H2aa, P-Npm (KOBAN), and three MEFs infected control vector, were used. RNA was extracted from iPS clones at passage 3 or 4. RNA was extracted from MEFs 4 days after infection. b), Gene expression profiling. Relative expression levels of Klf-4/Oct3/4/H2aa/H2ba/P-Npm2 (KOBAN)-induced pluripotent stem cell clones compared to MEFs, Yamanaka four factors-induced iPSCs, or ES cells. c), DNA methylation analysis of endogenous pluripotency marker gene promoters and a imprinted gene. The methylation state of the Nanog and Pou5f1 promoters and Snrpn imprinted locus in early-passage (passage 3 or 4) of iPS cells was analysed using bisulfite sequencing. Open circles indicate unmethylated CpG dinucleotides and filled circles indicate methylated CpG dinucleotids.

Figure 6:
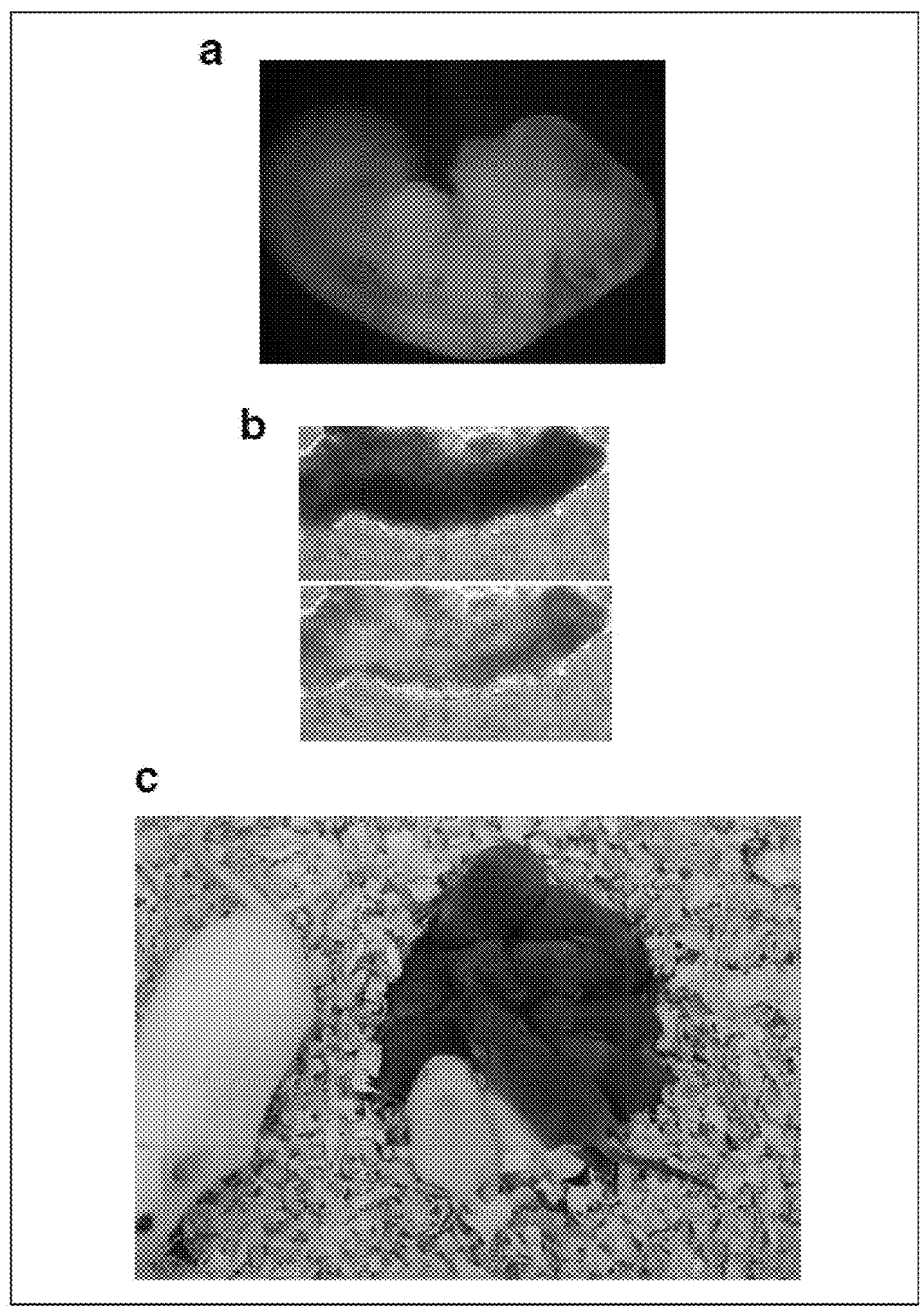

FIG. 6 shows a chimeric mouse generated so as to show that a nuclear reprogrammed cell obtained in the Examples of the present invention has a pluripotency. a), Contribution of iPSCs into multiple tissues. iPSCs were generated from MEFs, which expressed GFP constitutively, using Klf-4 and Oct3/4, H2aa, H2ba, and P-Npm2 (KOBAN) and then used for generation of chimeric mice. Image of GFP+ chimeric embryo at E12.5 is shown. b), Contribution of iPS cells into germ cells. Chimeric embryos were generated as described above, and image of gonadal tissues is shown. c), Contribution of iPSCs into germ line. Chimeric mice were generated as described above, and crossed with ICR mice. Representative images showing the contribution of iPSCs to chimeric coat in F2 offspring are indicated.

DESCRIPTION OF EMBODIMENTS

The following description specifically discusses an embodiment of the present invention.

[1. Generation Method for Generating Nuclear Reprogrammed Cell, Nuclear Reprogrammed Cell]

(Summary of the Generation Method)

A generation method in accordance with the present invention is a method for generating a nuclear reprogrammed cell from a somatic cell, and includes the step of introducing a given gene A and a nuclear reprogramming factor into an identical somatic cell. Note that the following description may refer to this step as an "introduction step" according to need.

(Gene A)

The gene A is at least one gene selected from the group consisting of:

(A1) a gene encoding histone H2aa, (A2) a gene encoding a homologue of histone H2aa, (A3) a gene encoding histone H2ba, (A4) a gene encoding a homologue of histone H2ba, (A5) a gene encoding a phosphorylation-mimic form of histone chaperon Npm2, and (A6) a gene conding a phosphorylation-mimic form of a homologue of histone chaperon Npm2.

In the present invention, a "gene" refers to a DNA or an RNA encoding a protein, a non-coding RNA (intended to include a microRNA (miRNA), for example) functioning in a cell, or a DNA encoding the non-coding RNA, unless otherwise noted. A use of a DNA as a gene has an advantage such that it is commonly easy to sustainably produce a gene product. Meanwhile, a use of an RNA as a gene has an advantage such that it is possible to produce a gene product without genetic modification. Note that a gene product refers to a protein or a non-coding RNA when a gene is a DNA, whereas a gene product refers to a protein when a gene is an RNA.

Histone H2aa, histone H2ba, and histone chaperon Npm2 which are mentioned above are all mouse-derived proteins, and examples of amino acid sequences of the respective proteins are published as respective accession numbers of NM__175658, NM__175663, and NM__181345.

A human-derived gene corresponding to the above (A2) is a gene (human gene name: Hist1h2aa) encoding histone protein TH2A. An example of an amino acid sequence of histone protein TH2A is published as an accession number of NM__170745. Similarly, a human gene corresponding to the above (A4) is a gene (human gene name: Hist1h2ba) encoding histone protein TH2B. An example of an amino acid sequence of histone protein TH2B is published as an accession number of NM__170610.

A phosphorylation-mimic form of histone chaperon Npm2 is obtained by substituting a glutamic acid or an aspartic acid for at least a part of putative phosphorylation sites (11 sites in total) of Npm2 so that the part of the putative phosphorylation sites of Npm2 are mimic phosphorylated.

A human gene corresponding to the above (A6) is designed in accordance with a sequence of human-derived histone chaperon Npm2 (hereinafter referred to as human Npm2) which is a human homologue of Npm2. An example of an amino acid sequence of human Npm2 is published as an accession number of NM__182795. Note that in the amino acid sequence, putative phosphorylation sites are fourth, fifth, seventh, eighth, ninth, 86th, 99th, 110th, 191st, 196th, and 204th amino acids.

Putative phosphorylation sites can be determined in histone chaperon Npm2 or a homologue thereof by a publicly-known method using software which analyzes a putative phosphorylation site (see the descriptions in the Examples). Meanwhile, in accordance with a publicly-known site-specific amino acid substitution introduction method (e.g., a Kunkel method or the like), a phosphorylation-mimic form can be obtained by substituting a glutamic acid or an aspartic acid for a putative phosphorylation site.

In a phosphorylation-mimic form of histone chaperon Npm2 or a phosphorylation-mimic form of a homologue of histone chaperon Npm2, a putative phosphorylation site is mimic phosphorylated (i.e., a glutamic acid or an aspartic acid is substituted therefor) in a ratio preferably of not less than 70%, more preferably of not less than 85% from the viewpoint of functional enhancement by mimic phosphorylation, and particularly preferably of 100% at which the putative phosphorylation site is completely mimic phosphorylated, with respect to the putative phosphorylation site.

Note that the gene encoding histone H2aa or a homologue thereof (the above (A1) or (A2)), the gene encoding histone H2ba or a homologue thereof (the above (A3) or (A4)), and the gene encoding histone chaperon Npm2 or a homologue thereof (the above (A5) or (A6)) are all high in expression in, for example, an oocyte, whereas these genes are comparatively low in expression in an ES cell (embryonic stem cell), and are hardly expressed in accordance with in vitro differentiation of the ES cell. Note also that, in a case where genes encoding histone H2aa, histone H2ba, and histone chaperon Npm2 (a non-phosphorylation-mimic form), respectively are coexpressed in a mouse somatic cell, a cell whose form is like an ES cell temporarily appears, but no cell that shows a long-term undifferentiated proliferation potency has been obtained.

(More Preferable Gene A or More Preferable Combination of Genes A)

For example, from the viewpoint of great efficiency in generation of a nuclear reprogrammed cell, it is preferable that at least the gene encoding a phosphorylation-mimic form of Npm2 (the above (A5)) or the gene encoding a phosphorylation-mimic form of a homologue of Npm2 (the above (A6)) be used as the gene A.

Note that any one of the genes A may be used alone. Alternatively, a use of a plurality of the genes A in combination may yield a remarkable effect.

For example, from the viewpoint of great efficiency in generation of a nuclear reprogrammed cell, it is preferable that at least the following genes (A7) and (A8) be used in combination as the gene (A).

(A7) a gene encoding histone H2aa or a homologue thereof (the above (A1) or (A2)), and (A8) a gene encoding histone H2ba or a homologue thereof (the above (A3) or (A4))

From the viewpoint of great efficiency in generation of a nuclear reprogrammed cell, it is preferable that the following three genes (A7) through (A9) be used in combination as the gene (A).

(A7) a gene encoding histone H2aa or a homologue thereof, (A8) a gene encoding histone H2ba or a homologue thereof, and (A9) a gene encoding a phosphorylation-mimic form of histone chaperon Npm2 or a phosphorylation-mimic form of a homologue of Npm2 (the above (A5) or (A6))

Namely, the generation method of the present invention using the gene A alone or a combination of the genes A can be viewed as a method for increasing efficiency in generation of a nuclear reprogrammed cell by causing a well-known nuclear reprogramming factor and the gene A to be coexpressed.

(Nuclear Reprogramming Factor)

A nuclear reprogramming factor refers to a factor which causes nuclear reprogramming of a somatic cell by being introduced into the somatic cell into which the gene A is introduced. The nuclear reprogramming factor may be a "gene", a gene product of the "gene" (a protein or an RNA encoded by the gene), or another factor (e.g., an agent or the like). The nuclear reprogramming factor is preferably a "gene" or a "protein", and more preferably a "gene".

The nuclear reprogramming factor as a gene is, for example, at least one gene selected from the group consisting of a Klf family gene, an Oct family gene, a Sox family gene, and a Myc family gene. Of these genes, it is preferable to use at least one of the Klf family gene and the Oct family gene.

The Klf family gene, which is exemplified by Klf1, Klf2, Klf4, Klf5, and the like, is preferably Klf4. Klf4 (Kruppel like factor-4) is reported as a tumor suppresor (reference: A. M. Ghaleb et al., Cell Res., 15, pp. 92-6, 2005).

The Oct family gene, which is exemplified by Oct3/4, Oct1A, Oct6, and the like, is preferably Oct3/4. Oct3/4 is a transcription factor belonging to a POU family, and is reported as an undifferentiation marker (reference: K. Okamoto et al., Cell, 60, pp. 461-72, 1990). Oct3/4 is also reported as being involved in sustaining a multipotency (reference: J. Nichols et al., Cell, 95, pp. 379-91, 1998).

The Sox family gene, which is exemplified by Sox1, Sox2, Sox3, Sox7, Sox15, Sox17, Sox18, and the like, is preferably Sox2. Sox2 is a gene which is expressed in an early development process and encodes a transcription factor (reference: A. A. Avilion et al., Genes Dev., 17, pp. 126-40, 2003).

The Myc family gene is exemplified by c-Myc, N-Myc, L-Myc, and the like. c-Myc, which is a transcriptional repressor involved in cell differentiation and cell proliferation (reference: S. Adhikary, M. Eilers, Nat. Rev. Mol. Cell Biol., 6, pp. 635-45, 2005), is reported as being involved in sustaining a multipotency (reference: P. Cartwright et al., Development, 132, pp. 885-96, 2005). Note that cytokine can be substituted for an expression product of the Myc family gene in some cases. Cytokine is, for example, preferably SCF, bFGF, or the like, and more preferably bFGF. However, cytokine is not limited to these.

International Publication WO2007/69666 (reference) shows specific examples of the Oct family gene, the Klf family gene, the Sox family gene, and the Myc family gene which are described above.

Another example of the nuclear reprogramming factor as a gene is a factor to be used to establish an iPS cell, and is exemplified by a Lin family gene, a Nanog gene, a Tbx family gene (reference: Nature. 2010 Feb. 25; 463 (7284): 1096-100.), a UTF1 gene (reference: Cell Stem Cell. 2008 Nov. 6; 3(5): 475-9), a SALL family gene (reference: Tsubooka et al., Genes Cells. 2009 June; 14(6): 683-94. Epub 2009 May 19.), an Nr5a2 gene, an Nr5a1 gene, an Nr1i2 gene (reference: Heng et al., Cell Stem Cell. 2010 Feb. 5; 6(2): 167-74.), a Rem2 GTPase gene (reference: Edel et al., Genes Dev. 2010 Mar. 15; 24(6): 561-73.), a TCL-1A gene (reference: Picanco-Castro et al., Stem Cells Dev. 2010 January; 20(1): 169-80.), an Esrr family gene (reference: Feng et al., Nat Cell Biol. 2009 February; 11(2): 197-203), a Prmt5 gene (reference: Nagamatsu et al., J Biol Chem. 2011 Mar. 25; 286(12): 10641-8.), a Glis family gene (reference: Maekawa et al., Nature. 2011 Jun. 8; 474(7350): 225-9.), and the like; and genes similar to these genes.

The Lin family gene is exemplified by, for example, Lin28, Lin28B, and the like. The Tbx family gene is exemplified by, for example, Tbx3 and the like. The SALL family gene is exemplified by, for example, SALL4 and the like. The Esrr family gene is exemplified by, for example, Esrrb, Esrrg, and the like. The Glis family gene is exemplified by, for example, Glis1, Glis2, Glis3, and the like.

Further, other examples of the nuclear reprogramming factor as a gene include miR-291-3p, miR-294, and miR-295 (reference: Judson et al., Nat Biotechnol. 2009 May; 27(5): 459-61.); miR-17-92, miR-106b-25, miR106a-363, miR-93, and miR-106b (reference: Li et al., EMBO J. 2011 Mar. 2; 30(5): 823-34); an mir-302 family miRNA (reference: Kamata et al., PloS One. 2010 Jul. 28; 5(7): e11834, Lin et al., Nucleic Acids Res. 2011 February; 39(3): 1054-65.); mir-200c, mir-302s, and mir-369s family miRNAs (reference: Miyoshi et al., Cell Stem Cell. 2011 Jun. 3; 8(6): 633-8.); and the like, each of which is an ES cell-specific miRNA.

Further, the another factor is exemplified by low molecular weight compounds to be used to establish an iPS cell such as an arginine methyltransferase (PRMT) inhibitor, a TGF-β inhibitor, a GSK3 inhibitor, and a lysine-specific demethylase 1 (LSD1) inhibitor; siRNA against a p53 gene; and the like (references: Shi et al., Cell Stem Cell. 2008 Jun. 5; 2(6): 525-8., Huangfu et al., Nat Biotechnol. 2008 Jul. 26(7): 795-7, Huangfu et al., Nat Biotechnol. 2008 November; 26(11): 1269-75. Mali et al., Stem Cells. 2010 Apr., 28(4): 713-20, Liang et al., J Biol Chem. 2010 Aug. 13; 285(33): 25516-21, Zhu et al., Cell Stem Cell. 2010 Dec. 3; 7(6): 651-5, Marson et al., Cell Stem Cell. 2008 Aug. 7; 3(2): 132-5, Li et al., Stem Cells. 2009 December; 27(12): 2992-3000., Zhao et al., Cell Stem Cell. 2008 Nov. 6; 3(5): 475-9, Theunissen et al., Curr Biol. 2011 Jan. 11; 21(1): 65-71., Xu et al., Proc Natl Acad Sci USA. 2010 May 4; 107(18): 8129-34., Hanna et al., Nature. 2009 Dec. 3; 462(7273): 595-601., Guo et al., Development. 2009 April; 136(7): 1063-9., Lyssiotis et al., Proc Natl Acad Sci USA. 2009 Jun. 2; 106(22): 8912-7., Li et al., Hum Mol Genet. 2009 Nov. 15; 18(22): 4340-9., Taeknaka et al., Exp Hematol. 2010 February; 38(2): 154-62., Maherali and Hochendlinger, Curr Biol. 2009 Nov. 3; 19(20): 1718-23., Ichida et al., Cell Stem Cell. 2009 Nov. 6; 5(5): 491-503., Chen et al., Stem Cells. 2010 August; 28(8): 1315-25., Chen et al., Aging Cell. 2011 October; 10(5):908-11. doi: 10.1111/j.1474-9726.2011.00722.x. Epub 2011 Jun. 14., Zhang et al., Stem Cells. 2011 February; 29(2): 229-40., Li et al., Cell Stem Cell. 2010 Oct. 8; 7(4): 508-20., Li et al., EMBO J. 2011 Mar. 2; 30(5): 823-34, etc.).

Nuclear reprogramming factors as proteins correspond to proteins encoded by the nuclear reprogramming factors as genes. Of these nuclear reprogramming factors as proteins, it is preferable to use at least one of a Klf family protein and an Oct family protein. Note that wild-type, variant, or both wild-type and variant nuclear reprogramming factors can be used as both the nuclear reprogramming factors as proteins and the nuclear reprogramming factors as genes.

(Preferable Combination of Nuclear Reprogramming Factors)

Any one of the above nuclear reprogramming factors may be used alone. Alternatively, a use of a plurality of the nuclear reprogramming factors in combination may yield a remarkable effect.

It is possible to take, as an example, introduction of the Klf family gene (e.g., a Klf4 gene) and the Oct family gene (e.g., an Oct3/4 gene) as the nuclear reprogramming factors into a somatic cell so that these genes can be expressed. Similarly, it is also possible to take, as an example, introduction of the Klf family protein (e.g., Klf4) and the Oct family protein (e.g., Oct3/4) as the nuclear reprogramming factors into a somatic cell. According to this, a use of the nuclear reprogramming factors and the given gene A in combination remarkably increases efficiency in generation of a nuclear reprogrammed cell (also see the Examples). Further, it is unnecessary to use the Myc family gene or protein which is said to have the possibility of causing cancer.

It is possible to take, as another example, introduction of the Klf family gene (e.g., a Klf4 gene), the Oct family gene (e.g., an Oct3/4 gene), the Sox family gene (e.g., a Sox2 gene), and the Myc family gene (e.g., a c-Myc gene) as the nuclear reprogramming factors into a somatic cell so that these genes can be expressed. Similarly, it is also possible to take, as another example, introduction of the Klf family protein (e.g., Klf4), the Oct family protein (e.g., Oct3/4), the Sox family protein (e.g., Sox2), and the Myc family protein (e.g., a c-Myc protein) as the nuclear reprogramming factors into a somatic cell. According to this, a use of the nuclear reprogramming factors and the given gene A in combination remarkably increases efficiency in generation of a nuclear reprogrammed cell (also see the Examples).

In a case where any one of the nuclear reprogramming factors is used alone, it may be preferable to select a somatic cell at interest which is at a more advanced stage in a reprogramming process. For example, it is possible to select, as the somatic cell, a neural stem cell (reference: Kim et al., Cell. 2009 Feb. 6; 136(3): 411-9., Kim et al., Nature. 2009 Oct. 1; 461 (7264): 649-3.) or the like.

Note that in the present invention, "nuclear reprogramming" or "reprogramming a nucleus" most broadly means causing a somatic cell at interest to be at a cell differentiation level at an earlier stage (including an undifferentiated state). "Nuclear reprogramming" or "reprogramming a nucleus" is exemplified preferably by causing a somatic cell at interest to be in a state in which the somatic cell at interest shows a multipotency or a state earlier than this state, and more preferably by causing a somatic cell at interest to be in a state in which the somatic cell at interest shows a pluripotency or a state earlier than this state. Note that in the present invention, the multipotency refers to a capability of differentiating into a part of cell lineages such as a neural cell, a hematopoietic cell, or the like. Note also that in the present invention, the pluripotency refers to a capability of constituting no individual itself but differentiating into all the cells and tissues each constituting an individual.

Similarly, in the present invention, a "nuclear reprogrammed cell" refers to a cell obtained by "nuclear reprogramming" a somatic cell at interest. An example of the "nuclear reprogrammed cell" is a so-called "induced pluripotent stem cell". The "induced pluripotent stem cell" refers to a cell which is similar in property to an ES cell (embryonic stem cell). More specifically, the "induced pluripotent stem cell" encompasses a cell which is an undifferentiated cell and has a pluripotency and an undifferentiated proliferation potency depending on a culturing condition.

(Somatic Cell)

In the present invention, a "somatic cell" to be subjected to nuclear reprogramming is not particularly limited in type, derivation, and the like, and any somatic cell can be used. As for types of cells, any cells, but other than germ cells can be somatic cells. Examples of such cells include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), contractile cells (e.g., smooth muscle cells), cells of the blood and the immune system (e.g., T lymphocytes), sense-related cells (e.g., rod cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells thereof (tissue progenitor cells) and the like. There is no limitation on the degree of cell differentiation; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as nerve stem cells, hematopoietic stem cells, mesenchymal stem cells, and dental pulp stem cells.

Examples of a preferable embodiment of somatic cells include fibroblasts, synovial cells, keratinocytes, amniocytes, endometrial cells, glia cells, astrocytes, meningeal cells, marrow-derived myeloid cells, peripheral blood-derived CD34 positive blood cells, marrow mononuclear cells, T cells, natural killer cell lymphoma, natural killer T cells, B lymphocytes, umbilical vein endothelial cells, pancreatic β cells, testis-derived cells, tooth germ-derived cells, mesenterium-derived cells, neural stem cells, blood stem cells, hepatic stem cells, adipose-derived stem cells, and the like, in each of which an induced pluripotent stem cell is reported to be established. The somatic cells may be either primary cultured cells or subcultured cells. For example, the somatic cells may derive from not only prenatal (fetal) individuals but also matured individuals.

Animal species from which somatic cells derive are not particularly limited, either. In view of industrial application to, for example, a cell therapy/tissue therapy, mammal (mammalian)-derived somatic cells are preferable. Examples of mammalians, which are not particularly limited in type, include laboratory animals such as mice, rats, rabbits, guinea pigs, primates except human beings, and the like; pets such as dogs, cats, and the like; domestic animals such as cattle, horses, and the like; and human beings. A human-derived tissue or cell is preferable especially for clinical application.

Either a somatic cell having differentiated from a cell nuclear reprogrammed by the present invention or a somatic cell having differentiated from an iPS cell established by a prior technique can also be treated as a "somatic cell" to be subjected to nuclear reprogramming by the present method. A preferable embodiment of the somatic cell is similar to that described above.

In order to use, for a disease treatment, a nuclear reprogrammed cell obtained by nuclear reprogramming a somatic cell, it may be desirable in one aspect to use a somatic cell separated from a patient's own cell. For example, it is possible to use a somatic cell involved in a disease, a somatic cell involved in a disease treatment, or the like.

Though not particularly limited, it is preferable to determine, in accordance with an animal species from which the somatic cell derives, derivations of the gene A and the nuclear reprogramming factor (in case of a gene or a protein) which are to be used. For example, in a case where a mouse-derived somatic cell is used as the somatic cell, it is preferable to use a mouse-derived (same animal-derived) gene and a mouse-derived (same animal-derived) nuclear reprogramming factor or altered forms thereof as the gene A and the nuclear reprogramming factor (in case of a gene or a protein). Meanwhile, in a case where a human-derived somatic cell is used as the somatic cell, it is preferable to use a human-derived gene and a human-derived nuclear reprogramming factor or altered forms thereof as the gene A and the nuclear reprogramming factor (in case of a gene or a protein).

(Summary of Introduction Step)

In the introduction step, the given gene A and the nuclear reprogramming factor are introduced into an identical somatic cell. For example, the gene A and the nuclear reprogramming factor are introduced into a somatic cell by use of a publicly-known method in a culture environment in which a somatic cell and a nuclear reprogrammed cell can be proliferated and maintained. Note that examples of the culture environment in which a somatic cell and a nuclear reprogrammed cell can be proliferated and maintained include various culture environments employed in generation of an induced pluripotent stem cell and culture environments obtained by altering the various culture environments (also see the Examples).

The gene A is introduced into the somatic cell by use of, for example, a vector which contains the gene A so that the gene A can be expressed. It is only necessary that a type of the vector be appropriately selected in accordance with a type of the somatic cell. The vector is exemplified by a plasmid vector, a viral vector (preferably an adenoviral vector, a retroviral vector, and the like), and the like.

A method for introducing the vector into the somatic cell is exemplified by an electroporation method (Nucleic, Acids Res. 15, 1311-1326 (1987)), a calcium phosphate method (Mol. Cell Biol. 7, 2745-2752 (1987)), a lipofection method (Cell 7, 1025-1037 (1994); Lamb, Nature Genetics 5, 22-30 (1993)), and the like.

In a case where a combination of a plurality of types of genes is used as the gene A, these plurality of types of genes may be incorporated into an identical vector or different vectors. Further, these plurality of types of genes may be introduced into the somatic cell simultaneously or at different timings.

In a case where the nuclear reprogramming factor is a gene, it is only necessary that the nuclear reprogramming factor be introduced into the somatic cell as in the case of the gene A. Meanwhile, in a case where the nuclear reprogramming factor is a protein, it is possible to employ the following method: (i) a method in which the nuclear reprogramming factor is added to a culture medium in which the somatic cell is cultured, so as to cause the nuclear reprogramming factor to be incorporated into the somatic cell (see, for example, references: Zhou et al., Cell Stem Cell. 2009 May 8; 4(5): 381-4., Kim et al., Cell Stem Cell. 2009 Jun. 5; 4(6): 472-6., Japanese Patent Application Publication, Tokukai, No. 2010-110289 A (Publication Date: May 20, 2010), and Japanese Patent Application Publication, Tokukai, No. 2010-252786 A (Publication Date: Nov. 11, 2010); or (ii) a method in which in addition to the somatic cell to be subjected to nuclear reprogramming, a somatic cell rich in nuclear reprogramming factors (e.g., a cell in which nuclear reprogramming factors are overexpressed) is prepared and these somatic cells are fused by a cell fusion technique. In a case where the cell fusion technique is used, it is preferable to control a nucleus of the somatic cell rich in nuclear reprogramming factors so as to prevent the nucleus from being incorporated into the somatic cell to be subjected to nuclear reprogramming. In a case where the nuclear reprogramming factor is neither a gene nor a protein but another factor (e.g., an agent or the like), it is only necessary that the nuclear reprogramming factor be added to a culture medium in which the somatic cell is cultured, so as to cause the nuclear reprogramming factor to be incorporated into the somatic cell.

Note that a timing at which the gene A and the nuclear reprogramming factor are introduced into an identical somatic cell is not particularly limited. The gene A and the nuclear reprogramming factor may be introduced into the identical somatic cell simultaneously or at different timings.

(Another Step in the Generation Method for Generating Nuclear Reprogrammed Cell of the Present Invention)

The generation method for generating a nuclear reprogrammed cell in accordance with the present invention can further include a proliferation step of culturing a somatic cell (nuclear reprogrammed cell) having been subjected to the process described earlier in the introduction step, and subjecting the somatic cell to undifferentiated proliferation. For example, the culture environment described earlier in the introduction step can be used as it is for a culture environment in which the proliferation step is carried out.

A nuclear reprogrammed cell having appeared in a culture medium by carrying out the generation method for generating a nuclear reprogrammed cell in accordance with the present invention may be separated from a cell other than the nuclear reprogrammed cell by being subjected to a separation step according to need. A method for carrying out the separation step is not particularly limited. For example, as the method for carrying out the separation step, it is possible to appropriately employ the following means: (i) means for separating the nuclear reprogrammed cell by using a drug resistance gene or the like as a marker gene and taking a drug resistance as an indicator; (ii) means for separating the nuclear reprogrammed cell by taking a morphological characteristic as an indicator; (iii) means for separating the nuclear reprogrammed cell by taking, as an indicator, whether or not a given marker is expressed or in what amount of the given marker is expressed; or (iv) the like. Various culture media in each of which an undifferentiated property and a multipotency of an ES cell can be sustained or cannot be sustained are known, and a use of appropriate culture media in combination may allow efficient separation of a nuclear reprogrammed cell. A differentiation potency and an undifferentiated proliferation potency of the separated nuclear reprogrammed cell can be easily checked by use of checking means generally used for an ES cell.

(Cell Obtained by the Generation Method of the Present Invention)

A nuclear reprogrammed cell in accordance with the present invention is generated by the above generation method. An example of the nuclear reprogrammed cell is a so-called "induced pluripotent stem cell". The "induced pluripotent stem cell" refers to a cell which is similar in property to an ES cell (embryonic stem cell). More specifically, the "induced pluripotent stem cell" encompasses a cell which is an undifferentiated cell and has a pluripotency and an undifferentiated proliferation potency depending on a culturing condition.

The present invention encompasses a somatic cell obtained by causing differentiation of a nuclear reprogrammed cell generated by the above generation method. It is only necessary to appropriately employ, as a method for causing differentiation of the nuclear reprogrammed cell, a technique established as a method for inducing a desired differentiated cell (e.g., a nerve cell, a cardiomyocyte, a hemocyte cell, a neural stem cell, a hematopoietic stem cell, or the like) from an ES cell or an induced pluripotent stem cell, e.g., a method in which the nuclear reprogrammed cell is treated with a retinoic acid, a growth factor such as EGF, glucocorticoid, or the like.

A nuclear reprogrammed cell and a somatic cell which have been generated by the method of the present invention are not particularly limited in use. For example, the nuclear reprogrammed cell and the somatic cell can be used for tests and research similar to those on an ES cell, screening of an agent (a hepatic somatic cell), a cell therapy/a tissue therapy (an autologous cell/an autologous tissue transplantation, an allogenic cell/an allogenic tissue transplantation), and the like.

[2. Screening Method for Screening Nuclear Reprogramming Factor]

(Summary of the Screening Method)

A screening method in accordance with the present invention for screening a nuclear reprogramming factor includes the steps of:

1) preparing a somatic cell into which at least one given gene A mentioned above is introduced so as to be expressed;

2) introducing a candidate for the nuclear reprogramming factor into a somatic cell or bringing the candidate for the nuclear reprogramming factor into contact with the somatic cell; and 3) determining whether or not the somatic cell has been nuclear reprogrammed after the steps 1) and 2) have been carried out.

Note that the somatic cell in the step 1) and the somatic cell in the step 2) are identical.

Note that definitions of the "somatic cell" and the "gene A" in the step 1), and a method for introducing the "gene A" into the somatic cell are as described earlier in the section [1. Generation Method for Generating Nuclear Reprogrammed Cell, Nuclear Reprogrammed Cell]. A preferable combination of a plurality of types of genes A is also as described earlier in the in the section [1. Generation Method for Generating Nuclear Reprogrammed Cell, Nuclear Reprogrammed Cell].

The "candidate for the nuclear reprogramming factor" in the step 2) broadly refers to a factor which (i) is introduced into a somatic cell into which the gene A is introduced and (ii) may cause nuclear reprogramming to the somatic cell. The candidate for the nuclear reprogramming factor may be a "gene", a gene product of the "gene", or another factor (e.g., an agent or the like). The candidate for the nuclear reprogramming factor is preferably a "gene" or a "protein", and more preferably a "gene".

Examples of the "candidate for the nuclear reprogramming factor" include a gene cluster which is reported to be specifically expressed in an oocyte or an ES cell, a gene product encoded by the gene cluster, an agent which may be involved in reprogramming (e.g., an histone deacetylase inhibitor or the like), and the like.

Note that the scope of the present invention encompasses a technique for carrying out the screening method by using, as the "candidate for the nuclear reprogramming factor", various genes, proteins, or other factors each of which is described earlier as the nuclear reprogramming factor, and determining whether or not the screening method appropriately functions. In this case, it is only necessary that the candidate for the nuclear reprogramming factor be introduced into or brought into contact with the somatic cell in accordance with the method described earlier in the section [1. Generation Method for Generating Nuclear Reprogrammed Cell, Nuclear Reprogrammed Cell].

For example, as the step 3), it is possible to appropriately employ the following means: (i) means for determining, by taking a morphological characteristic as an indicator, whether or not a cultured cell having been subjected to the steps 1) and 2) contains a nuclear reprogrammed cell; (ii) means for determining, by taking, as an indicator, whether or not a given marker (e.g., a Nanog gene) is expressed or in what amount the given marker is expressed, whether or not a cultured cell having been subjected to the steps 1) and 2) contains a nuclear reprogramming cell; or (iii) the like. Various culture media in each of which an undifferentiated property and a multipotency of an ES cell can be sustained or cannot be sustained are known, and a use of appropriate culture media in combination may allow efficient determination of presence/absence of a nuclear reprogrammed cell.

In a case where a nuclear reprogrammed cell is generated in the cultured cell, it is determined in the step 3) that the candidate for the nuclear reprogramming factor serves as the nuclear reprogramming factor.

Note that according to the screening method in accordance with the present invention, an order in which the step 1) and the step 2) are carried out is not particularly limited. The steps 1) and 2) may be carried out simultaneously or at different timings.

(Cell Suitably Used for Screening)

From the viewpoint of enhancement of a screening sensitivity, a cell described in the following 1) or 2) is preferable, and the cell described in 2) is more preferable in the screening method in accordance with the present invention.

1) A cell obtained in a case where as the gene A, at least a gene encoding mimic phosphorylated histone chaperon Npm2 or a homologue thereof is introduced into a somatic cell so that the gene can be expressed.

2) A cell obtained in a case where as the gene A, all a gene encoding histone H2aa or a homologue thereof, a gene encoding histone H2ba or a homologue thereof, and a gene encoding mimic phosphorylated Npm2 or a homologue thereof are introduced into a somatic cell so as to be expressed.

Note that definitions of the "somatic cell" and the "gene A", and a method for introducing the "gene A" into the somatic cell are as described earlier in the section [1. Generation Method for Generating Nuclear Reprogrammed Cell, Nuclear Reprogrammed Cell].

[3. Inducer of Nuclear Reprogramming]

An inducer of nuclear reprogramming in accordance with the present invention is an agent which induces nuclear reprogramming of a somatic cell and contains at least one of the genes A and a gene encoding the nuclear reprogramming factor (but limited to a protein).

Note that all the at least one of the genes A and the gene encoding the nuclear reprogramming factor each of which is contained in the inducer may be loaded on an identical vector or a part of the genes may be loaded on a different vector.

Examples

Expression of Two Histone Variants in Oocytes and Testis

Figure 2:
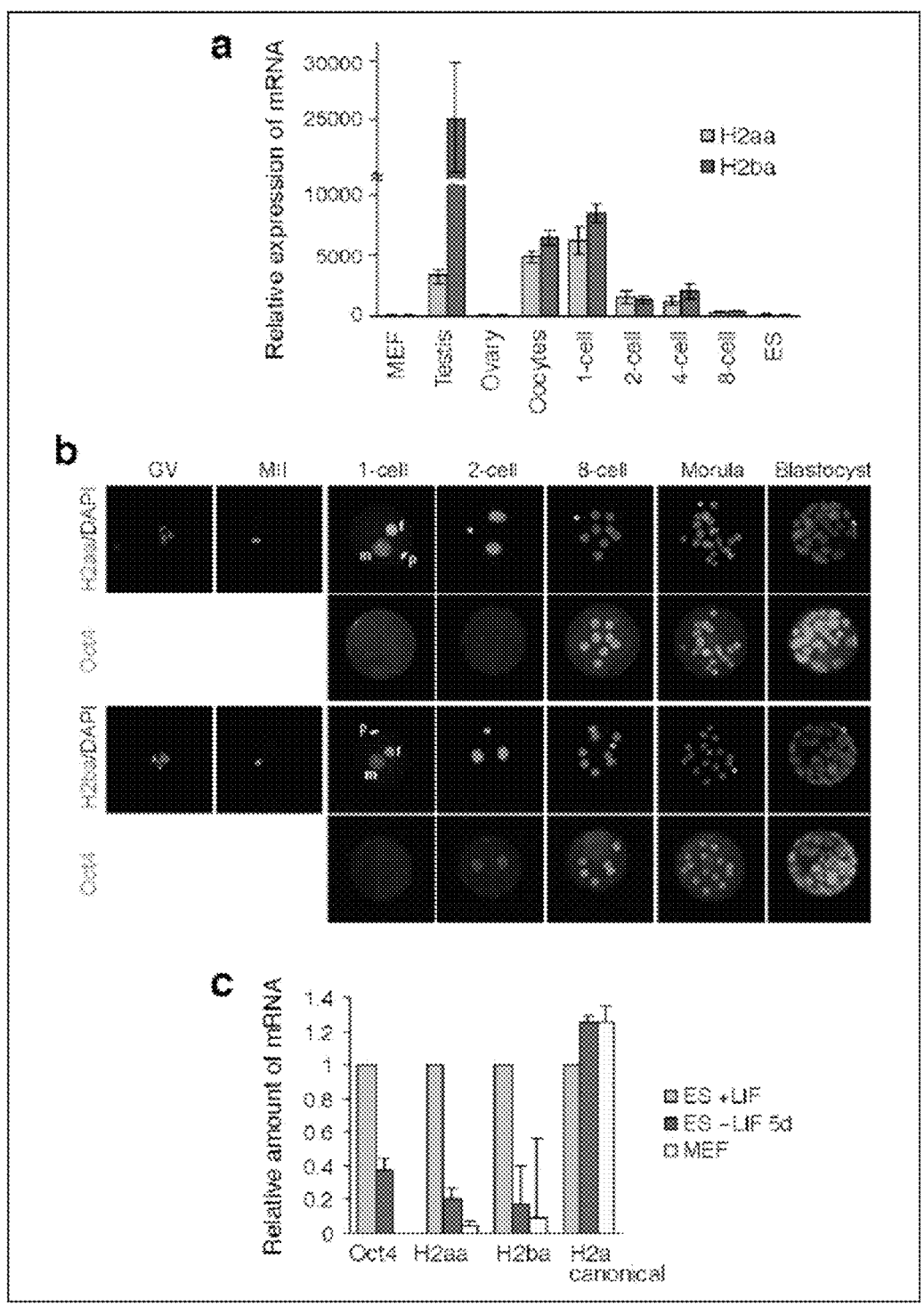
FIG. 2 is a graph showing expression levels (levels of transcription to mRNA) of histone H2aa and histone H2ba in various tissues and cells of a mouse. a), Relative expression levels of H2aa and H2ba mRNA were measured using qRT-PCR. b), Immunofluorescence images of H2aa/H2ba-stained oocytes and embryos. H2aa and H2ba were stained in red, while Oct4 was stained in green. DAPI staining marks chromatin in blue. m: male pronucleus, f: female pronucleus, p: polar body. c), H2aa and H2ba are expressed in undifferentiated ES cells. ES cells were cultured for 5 days in the presence or absence of the LIF and mRNA levels were measured by qRT-PCR.

Two histone variants, H2aa (Accession no. AAO06231) and H2ba (Accession no. CAA62299), have the 15- and 16-amino acid difference compared to canonical somatic cell histones, H2A (H2ao, Accession no. AAO06223) and H2B (H2bf, Accession no. AAO06245) (FIG. 1) (Marzluff, W. F., Gongidi, P., Woods, K. R., Jin, J. & Maltais, L. J. The human and mouse replication-dependent histone genes. *Genomics* 80, 487-498 (2002).). Rat homologues of these variants were originally called as TH2A and TH2B, respectively, due to their enrichment in the testis (Trostle-Weige, P. K., Meistrich, M. L., Brock, W. A., Nishioka, K. & Bremer, J. W. Isolation and characterization of TH2A, a germ cell-specific variant of histone 2A in rat testis. J. Biol. Chem. 257, 5560-5567 (1982).; Brock, W. A., Trostle, P. K. & Meistrich, M. L. Meiotic synthesis of testis histones in the rat. Proc. Natl. Acad. Sci. USA 77, 371-375 (1980)). Inventors have examined the mRNA levels of these variants during development. The high levels of mRNA were found not only in the testis but also in the oocytes (FIG. 2a). Significant levels of mRNA were detected in the fertilized eggs, and their levels gradually decreased during differentiation into inner cell mass (FIG. 2a).

Immunostaining with the H2aa- and H2ba-specific antibodies indicated that strong signals of both variants were evident at the rim surrounding nucleolus and nuclear dot-liked-domains in the germinal vesicle (GV) of oocytes and also in the metaphase II-stage oocytes (MII) (FIG. 2b).

H2aa were detected both in the nucleoplasm and in the nucleoli of fertilized 1-cell embryo, but H2ba was excluded from the nucleoli. Consistent with the mRNA data, significant immunostaining signals in the fertilized eggs decreased during differentiation into ICM (FIG. 2b). Low levels of mRNA of these two variants were detected in ES cells, which then became undetectable during differentiation upon removal LIF (FIG. 2c). These data suggest a possible linkage between the expression of these histone variants and the pluripotency or multipotency of cells. H2aa and H2ba enhanced iPSCs generation by Yamanaka four factors Histone chaperon functions to recruit histone molecules into nucleosome (Avvakumov, N., Nourani, A, & Côté, J. Histone chaperones: modulators of chromatin marks. Mol. Cell 41, 502-514 (2011)), and we speculated that deposition of these histone variants might require specific histone chaperon. It was reported that nucleoplasmin (Npm2), one of the histone chaperon, is highly expressed in oocytes (Bürglin, T. R., Mattaj, I. W., Newmeyer, D. D., Zeller, R. & De Robertis, E. M. Cloning of nucleoplasmin from *Xenopus laevis* oocytes and analysis of its developmental expression. Genes Dev. 1, 97-107 (1987)), and that Npm2 contributes to in vitro decondensation of the chromatin from *Xenopus* somatic cells (Tamada, H., Van Thuan, N., Reed, P., Nelson, D., Katoku-Kikyo, N., Wudel, J., Wakayama, T. & Kikyo, N. Chromatin decondensation and nuclear reprogramming by nucleoplasmin. Mol. Cell. Biol. 26, 1259-1271 (2006)). Furthermore, Npm2 is highly phosphorylated in the oocytes and its phosphorylation is required for decondensation activity (Bañuelos, S. et al. Phosphorylation of both nucleoplasmin domains is required for activation of its chromatin decondensation activity. J. Biol. Chem. 282, 21213-21221 (2007)). Inventors have generated the expression vectors for phosphorylation-mimicform of Npm2 (P-Npm2), in which 11 different putative phosphorylation sites were changed to Asp. When two histone variants were coexpressed with P-Npm2 using the retrovirus vectors, the GFP-positive iPSC colonies appeared earlier compared to the case in which only Yamanaka four factors were used (FIG. 3a). To accurately measure the number of GFP-positive iPSCs, all cells were trypsinyzed and analyzed by FACS10 days after infection of viruses (FIG. 3b). The efficiency of iPSC generation by Yamanaka four factors was enhanced about 8.7-fold by H2aa and H2ba, although either of those variants did not significantly stimulate (FIG. 3c). Coexpression of both two histone variants and P-Npm2 further enhanced the efficiency of iPSC generation by Yamanaka four factors about 18-fold (FIG. 3c). Thus, H2aa, H2ba, and P-Npm2 greatly enhanced iPSC generation from somatic cells.

Generation of iPSCs Using Two Histone Variants without C-Myc and Sox-2

Inventors then attempted to remove some of the Yamanaka four factors in the reprogramming assays. H2aa, H2ba, and P-Npm2 did not enhance the iPSC generation by three Yamanaka factors (Klf-4, Oct3/4, and Sox-2) from MEFs (FIG. 4a), although these three Yamanaka factors produced significant number of iPSCs as reported (Nakagawa, M., Koyanagi, M., Tanabe, K., Takahashi, K., Ichisaka, T., Aoi, T., Okita, K., Mochiduki, Y., Takizawa, N. & Yamanaka, S. Generation of induced pluripotent stem cells without Myc from mouse and human fibroblasts. Nat. Biotechnol. 26, 101-106 (2008)). Removal of either Klf-4 or Oct3/4 from Yamanaka four factors did not generate iPSCs, and addition of H2aa, H2ba, and P-Npm2 did not allow to produce iPSCs (FIG. 4a). Interestingly, coexpression of H2aa, H2ba, and P-Npm2 with only two factors among Yamanaka four factors, Klf-4 and Oct3/4, generated significant number of iPSCs, although Klf-4 and Oct3/4 produced few number of iPSCs (FIG. 4b).

Note that it has been already confirmed that a proliferation potency of the generated iPS cells is sustained for at least four months.

Gene Expression Patterns and DNA Methylation Patterns of iPSCs Generated Using Two Histone Variants Using microarray analysis, genes expression patterns were compared between iPSCs generated using the two histone variants, Oct3/4, and Klf-4, iPSCs generated using Yamanaka four factors, ES cells, and MEFs. iPSCs generated using two histone variants, Oct3/4, and Klf-4 exhibited similar gene expression pattern with iPSCs generated by Yamanaka four factors and ES cells (FIG. 5a).

Analysis of DNA methylation status of Oct3/4 and Nanog gene promoter showed that these gene loci were hypomethylated in the iPSCs generated using the two histone variants, Oct3/4, and Klf-4, which is similar to ES cells. Thus, in iPSCs generated using two histone variants, Oct3/4, and Klf-4, the degree of DNA methylation of the ES cell-specific genes was down-regulated.

Pluripotency of iPSCs Generated Using Two Histone Variants

Inventors have tested the pluripotency of the iPSCs generated using two histone variants, Oct3/4, and Klf-4 by producing chimera mice. The iPSCs were produced from MEFs, which were prepared from the mice expressing GFP ubiquitously, and was used for chimera generation. The embryos at E12.5 exhibited GFP expression in various tissues from three germ layers (FIG. 6a, left). The E12.5 embryo also showed the GFP expression in the germ layer. These results indicate that the iPSCs generated using two histone variants, Oct3/4, and Klf-4 had the capacity to develop into various tissues, including germ cells.

To confirm the germ line transmission of the iPSCs generated using two histone variants, Oct3/4, and Klf-4, the obtained chimeric mice were mated with wildtype mice, and the chimerism of the generated mice were analyzed. The mice derived from the iPSCs, which were generated using two histone variants, Oct3/4, and Klf-4, were obtained (FIG. 6b). Thus, the iPSCs, which were generated using two histone variants, Oct3/4, and Klf-4, had the pluripotency.

Methods

Immunostaining of Oocytes and Early Embryos.

Oocytes and embryos were collected from superovulated ICR female mice and fixed with 2% PFA in PBS for 15 min at RT. After washing three times with PBS, the embryos were permeabilized with buffer containing 0.5% Triton X-100 and 0.5% BSA in PBS for 30 min at RT. They were washed three times with 0.5% BSA in PBS and stained with anti-H2aa-C (1:2,000) or anti-H2ba antibody (1:500) with anti-Oct3/4 antibody (1:500) (C-10, Santa cruz) for 2 h at RT. Anti-rabbit IgG Alexa568 and anti-mouse IgG Alexa488 (1:2,000) were used as second antibodies. After washing, the embryos were mounted in DAPI-containing Vectashield (H-1200, Vector Laboratories).

Generation of Antibodies Against Histone H2aa and H2ba.

The anti-H2aa-C rabbit antiserum was raised against an 11-mer peptide corresponding to residues 119-129 of the C-tail domain of histone H2aa. The anti-H2ba antiserum was raised against a 16-mer peptide corresponding to residues 3-18 of the N-tail domain of histone H2ba.

```
                                          (SEQ. ID NO. 1)
H2aa-C, 119-129 aa (11 aa), NH2-C+KKTESHKSQTK-COOH (SEQ. ID NO. 2)
H2ba: 3-18 aa (16 aa), NH2-EVAVKGATISKKGFKK+C-COOH
``` qRT-PCR.

Total RNA was isolated using Isogen (Nippon gene). qRT-PCR was performed with SuperScript III Platinum SYBR Green One-Step qRT-PCR Kit (Invitrogen). The equivalent of total RNA from 4 oocytes or embryos were used for each reaction. For tissues and cultured cells, 0.1 μg of total RNA were used. Primer sequences are supplied in Table 1.

Cell Culture.

Nanog-GFP MEFs were obtained from embryos (E14.5) of transgenic mice (Tg(Nanog-GFP,Puro)1Yam) (Okita, K., Ichisaka, T. & Yamanaka, S. Generation of germline-competent induced pluripotent stem cells. Nature 448, 313-317 (2007)). CAG-EGFP MEFs were obtained from C57BL/6-TgN(act-EGFP)OsbC14-Y01-FM131 mice (Okabe, M., Ikawa, M., Kominami, K., Nakanishi, T. & Nishimune, Y. 'Green mice' as a source of ubiquitous green cells. FEBS Lett. 407, 313-319 (1997)). MEFs and Plat-E cells were maintained in high-glucose DMEM containing 10% FBS, 100 U/ml penicillin/streptomycin. ESCs and iPS cells were maintained in knockout DMEM containing 15% knockout serum replacement (KSR) (Invitrogen), 1% FBS, 2 mM glutamine, 1% MEM non-essential amino acids, 100 μM β-mercaptoethanol, 1000 U/ml leukemia inhibitory factor (LIF), 50 U/ml penicillin/streptomycin on feeder layers of mitomycin C-treated MEFs.

Plasmid Construction.

H2aa and H2ba genes were amplified from mouse genomic DNA by PCR. H2ba and H2aa with IRES element in between were cloned in tandem into HpaI site of pDON-AI vector. H2aa and H2ba can be simultaneously expressed from this vector. Npm2 was amplified from ICR mouse oocyte RNA by using RT-PCR and cloned into pDON-AI. The choice of sites to be mutated in Npm2 was guided by data from *Xenopus* nucleoplasmin (Bañuelos, S. et al. Phosphorylation of both nucleoplasmin domains is required for activation of its chromatin decondensation activity. J. Biol. Chem. 282, 21213-21221 (2007)) and the prediction software KinasePhos (Huang, H.-D., Lee, T.-Y., Tzeng, S.-W. & Horng, J.-T. KinasePhos: a web tool for identifying protein kinase-specific phosphorylation sites. Nucleic Acids Res 33, W226-229 (2005)). A mutant Npm2 (N533) was obtained by PCR based site-directed mutagenesis. In N533, N-terminal 5 codons (5, 6, 7, 8, and 10), 3 codons (82, 95, and 104) at core domain, and C-terminal 3 codons (184, 189, and 197) were substituted for Asp: S5D, T6D, S7D, S8D, T10D, S82D, S95D, T104D, S184D, S189D, and T197D.

Retroviral Infection.

The day before transfection, PLAT-E cells were seeded at a density of $5 \times 10^6$ cells/10 cm dish. On the next day, medium was changed to 5 ml of opti-MEM containing 10% FBS. Retroviral vectors were introduced into PLAT-E cells using Fugene 6 transfection reagent (Roche). 27 μl of Fugene 6 transfection reagent was diluted in 150 μl of opti-MEM and incubated for 5 min. 9 μg of plasmid DNA was diluted in 150 μl of opti-MEM. Diluted Fugene 6 transfection reagent was added to diluted DNA and incubated for 15 min at room temperature (RT). After incubation, the DNA/Fugene 6 mixture was added drop by drop onto the Plat-E cells. Cells were then incubated at 37° C. with 5% $CO_2$. 6 to 12 h after transfection, 5 ml of DMEM containing 10% KSR was added. 48 h after transfection, virus-containing supernatants were collected and filtered through 0.45 μm Millex-HV (Millipore) filters and supplemented with 8 μg/ml of polybrene. The day before infection, MEFs were seeded at $1.6 \times 10^4$ cells/well of a 12-well plate for infection in the presence of 4 viral vectors expressing Klf4, Oct4, Sox2, and c-Myc (KOSM), or at $3.2 \times 10^4$ cells/well of a 12-well plate. In this study, we used MEFs within 3 passages to avoid replicative senescence. Virus containing supernatant was added onto the MEFs (day 0). Two days later (day 2), virus containing supernatant was removed and infected cells were cultured for 2 days in DMEM containing 10% KSR, 1% FBS and 100 U/ml penicillin/streptomycin. On day 4, cells (1/5 cells in the presence of KOSM) were passaged in a well of a gelatin-coated 6-well plate containing ES medium. Feeder cells ($8 \times 10^4$ cells/well) were added on the infected cells on day 5. The ES medium was changed every 2-3 days. Cells were maintained in culture until the appearance of GFP+ colonies.

FACS Analysis.

Medium was removed from cells and incubated with 0.4 mg/ml collagenase IV and 1 mM $CaCl_2$ in DMEM for 5 min at RT. The cells were washed with PBS and dissociated with accutase. The cells were passed through 40 μm nylon mesh to produce a single cell suspension. $1 \times 10^5$ cells was analysed by FACS.

Whole Genome Expression Analysis.

RNA samples to be analysed on microarrays were prepared using Isogen. 100 ng of total RNA was amplified and hybridized to the Mouse Gene 1.0 ST array (Affymetrix). Three biological replicates were included in the profiling of control vector or H2aa/H2ba/N533 induced MEFs. Statistical comparison of microarray expression datasets was performed in R (World Wide Web (www) r-project.org) using R commander interface. The quantile method implemented in the lumi package of RBioconductor was used to normalize the microarrays.

Bisulfite Genomic Sequencing.

Genomic DNAs (2 μg) from various cell lines were processed for bisulfite modification using EpiTect bisulfite kit (Qiagen). The promoter regions of Pou5f1 and Nanog and differently methylated region of Snrpn were amplified by PCR using primer sets provided in Table 1. The PCR products were cloned into pDON-AI vector using HindIII and EcoRI sites and sequenced.

Production of Chimeras.

Chimeras were generated by morula aggregation as described by Eakin et al. (Eakin, G. S. & Hadjantonakis, A.-K. Production of chimeras by aggregation of embryonic stem cells with diploid or tetraploid mouse embryos. Nat Protoc 1, 1145-1153 (2006)). In brief, ICR females were mated with ICR males. Eight-cell embryos were collected from oviducts of 2.5 day postcoital pregnant mice and 8-16 iPSCs were aggregated per 8-cell embryo. ICR mice were set up with vasectomized males and used as recipients for the aggregated embryos.

TABLE 1

| Gene | Forward | Reverse |
|---|---|---|
| qRT-PCR | | |
| H2aa | GGCTCGTGCCAAGGTCAA (SEQ. ID NO. 3) | GCACACGACCCACAGGAAAC (SEQ. ID NO. 4) |
| H2ao | ACGAGGAGCTCAACAAGCTG (SEQ. ID NO. 5) | TATTTTCCCT TGGCCTTGTG (SEQ. ID NO. 6) |
| H2ba | GACGTTGGTGTGGGAAAGGT (SEQ. ID NO. 7) | CCCTCCTTTTTCTGGGTCTT (SEQ. ID NO. 8) |
| Oct4 | CACGAGTGGAAAGCAACTCA (SEQ. ID NO. 9) | TTCATGTCCTGGGACTCCTC (SEQ. ID NO. 10) |
| Gapdh | ACTGGCATGGCCTTCCG (SEQ. ID NO. 11) | CAGGCGGCACGTCAGATC (SEQ. ID NO. 12) |
| Bisulfite sequencing | | |
| Nanog | agtgaagcttGATTTTGTAG (SEQ. ID NO. 13) GTGGGATTAATTGTGAATTT (SEQ. ID NO. 14) | gaattcACCAAAAAAACC (SEQ. ID NO. 15) CACACTCATATCAATATA (SEQ. ID NO. 16) |
| Pou5f1 | agtcaagcttGGTTGAG (SEQ. ID NO. 17) TGGGTTGTAAGGA (SEQ. ID NO. 18) | gaattcTCCAACCCTA (SEQ. ID NO. 19) CTAACCCATCACC (SEQ. ID NO. 20) |
| Snrpn | agtcaagcTTTAATGAGTGGG (SEQ. ID NO. 21) TAAAAGTAAGTATTGTATAG (SEQ. ID NO. 22) | gaaTTCTAATTTAAAACC (SEQ. ID NO. 23) TTAAAACTCTAACCCATA (SEQ. ID NO. 24) |
| pDON | GTTTTCCCAGTCACGACGTT (SEQ. ID NO. 25) | TGTGGAATTGTGAGCGGATA (SEQ. ID NO. 26) |

The invention is not limited to the description of the embodiments and examples above, but may be altered within the scope of the claims. An embodiment based on a proper combination of technical means disclosed in different embodiments is encompassed in the technical scope of the invention. Note that the descriptions in the references cited in the present specification are all quoted as a reference to the descriptions in the present specification.

INDUSTRIAL APPLICABILITY

The present invention makes it possible to provide a new method for generating a nuclear reprogrammed cell.

The invention claimed is:

1. A method for generating a nuclear reprogrammed cell from a mammalian somatic cell, said method comprising the step of:
introducing, into the mammalian somatic cell, (i) at least one gene selected from the group consisting of a gene encoding histone H2aa or TH2A, a gene encoding histone H2ba or TH2B, and a gene encoding a phosphorylation-mimic form of histone chaperon Npm2 or a phosphorylation-mimic form of human Npm2, and (ii) a nuclear reprogramming factor which is at least Klf family gene or gene product thereof and an Oct family gene or gene product thereof.

2. The method as set forth in claim 1, wherein as the at least one gene, at least the gene encoding a phosphorylation-mimic form of histone chaperon Npm2 or a phosphorylation-mimic form of human Npm2 is introduced into the mammalian somatic cell so as to be expressed.

3. The method as set forth in claim 1, wherein as the at least one gene, at least the gene encoding histone H2aa or TH2A and the gene encoding histone H2ba or TH2B are introduced into the mammalian somatic cell so as to be expressed.

4. The method as set forth in claim 2, wherein as the at least one gene, all the gene encoding histone H2aa or TH2A, the gene encoding histone H2ba or TH2B, and the gene encoding a phosphorylation-mimic form of histone chaperon Npm2 or a phosphorylation-mimic form of human Npm2 are introduced into the mammalian somatic cell so as to be expressed.

5. The method as set forth in claim 1, wherein the nuclear reprogramming factor which is introduced into the mammalian somatic cell so as to be expressed includes at least a Klf family gene and an Oct family gene.

6. The method as set forth in claim 5, wherein the Klf family gene is Klf-4, and the Oct family gene is Oct3/4.

7. The method as set forth in claim 1, wherein in the phosphorylation-mimic form of histone chaperon Npm2 or the phosphorylation-mimic form of human Npm2, a glutamic acid or an aspartic acid is substituted for all amino acids in phosphorylated sites of histone chaperon Npm2 or human Npm2.

8. The method as set forth in claim 1, wherein the mammalian somatic cell is a human cell.

9. A method for screening a nuclear reprogramming factor, said method comprising the steps of:
a) preparing a mammalian somatic cell into which at least one gene selected from the group consisting of a gene encoding histone H2aa or TH2A, a gene encoding histone H2ba or TH2B, and a gene encoding a phosphorylation-mimic form of histone chaperon Npm2 or a phosphorylation-mimic form of human Npm2 is introduced so as to be expressed;
b) introducing a candidate for the nuclear reprogramming factor into a mammalian somatic cell or bringing the candidate for the nuclear reprogramming factor into contact with the mammalian somatic cell; and
c) determining whether or not the mammalian somatic cell has been nuclear reprogrammed after the steps a) and b) have been carried out,
the mammalian somatic cell in the step a) and the mammalian somatic cell in the step b) being identical.

10. The method as set forth in claim 9, wherein into the mammalian somatic cell being obtained in the step a), at least the gene encoding a phosphorylation-mimic form of histone chaperon Npm2 or a phosphorylation-mimic form of human Npm2 is introduced so as to be expressed.

11. The method as set forth in claim 10, wherein into the mammalian somatic cell being obtained in the step a), all the gene encoding histone H2aa or TH2A, the gene encoding histone H2ba or TH2B, and the gene encoding a phosphorylation-mimic form of histone chaperon Npm2 or a phosphorylation-mimic form of human Npm2 are introduced so as to be expressed.

12. The method as set forth in claim 9, wherein the step b) is carried out by introducing a gene encoding the candidate for the nuclear reprogramming factor into the mammalian somatic cell.

13. An inducer from a mammalian somatic cell to a nuclear reprogrammed cell, comprising:
at least one gene selected from the group consisting of a gene encoding histone H2aa or TH2A, a gene encoding histone H2ba or TH2B, and a gene encoding a phosphorylation-mimic form of histone chaperon Npm2 or a phosphorylation-mimic form of human Npm2; and
a gene encoding a nuclear reprogramming factor which is at least Klf family gene or gene product thereof and an Oct family gene or gene product thereof.

* * * * *

```
                            SEQUENCE LISTING

<160> NUMBER OF SEQ ID NOS: 26

<210> SEQ ID NO 1
<211> LENGTH: 11
<212> TYPE: PRT
<213> ORGANISM: Mus musculus

<400> SEQUENCE: 1

Lys Lys Thr Glu Ser His Lys Ser Gln Thr Lys
1               5                   10

<210> SEQ ID NO 2
<211> LENGTH: 16
<212> TYPE: PRT
<213> ORGANISM: Mus musculus

<400> SEQUENCE: 2

Glu Val Ala Val Lys Gly Ala Thr Ile Ser Lys Lys Gly Phe Lys Lys
1               5                   10                  15

<210> SEQ ID NO 3
<211> LENGTH: 18
<212> TYPE: DNA
<213> ORGANISM: Artificial Sequence
<220> FEATURE:
<223> OTHER INFORMATION: forward primer

<400> SEQUENCE: 3
ggctcgtgcc aaggtcaa                                                 18

<210> SEQ ID NO 4
<211> LENGTH: 20
<212> TYPE: DNA
<213> ORGANISM: Artificial Sequence
<220> FEATURE:
<223> OTHER INFORMATION: reverse primer

<400> SEQUENCE: 4
gcacacgacc cacaggaaac                                               20

<210> SEQ ID NO 5
<211> LENGTH: 20
<212> TYPE: DNA
<213> ORGANISM: Artificial Sequence
<220> FEATURE:
<223> OTHER INFORMATION: forward primer

<400> SEQUENCE: 5
acgaggagct caacaagctg                                               20

<210> SEQ ID NO 6
<211> LENGTH: 20
<212> TYPE: DNA
<213> ORGANISM: Artificial Sequence
<220> FEATURE:
<223> OTHER INFORMATION: reverse primer

<400> SEQUENCE: 6
tattttccct tggccttgtg                                               20
```

```
<210> SEQ ID NO 7
<211> LENGTH: 20
<212> TYPE: DNA
<213> ORGANISM: Artificial Sequence
<220> FEATURE:
<223> OTHER INFORMATION: forward primer

<400> SEQUENCE: 7
gacgttggtg tgggaaaggt                                                   20

<210> SEQ ID NO 8
<211> LENGTH: 20
<212> TYPE: DNA
<213> ORGANISM: Artificial Sequence
<220> FEATURE:
<223> OTHER INFORMATION: reverse primer

<400> SEQUENCE: 8
ccctcctttt tctgggtctt                                                   20

<210> SEQ ID NO 9
<211> LENGTH: 20
<212> TYPE: DNA
<213> ORGANISM: Artificial Sequence
<220> FEATURE:
<223> OTHER INFORMATION: forward primer

<400> SEQUENCE: 9
cacgagtgga aagcaactca                                                   20

<210> SEQ ID NO 10
<211> LENGTH: 20
<212> TYPE: DNA
<213> ORGANISM: Artificial Sequence
<220> FEATURE:
<223> OTHER INFORMATION: reverse primer

<400> SEQUENCE: 10
ttcatgtcct gggactcctc                                                   20

<210> SEQ ID NO 11
<211> LENGTH: 17
<212> TYPE: DNA
<213> ORGANISM: Artificial Sequence
<220> FEATURE:
<223> OTHER INFORMATION: forward primer

<400> SEQUENCE: 11
actggcatgg ccttccg                                                      17

<210> SEQ ID NO 12
<211> LENGTH: 18
<212> TYPE: DNA
<213> ORGANISM: Artificial Sequence
<220> FEATURE:
<223> OTHER INFORMATION: reverse primer

<400> SEQUENCE: 12
caggcggcac gtcagatc                                                     18

<210> SEQ ID NO 13
<211> LENGTH: 20
<212> TYPE: DNA
<213> ORGANISM: Artificial Sequence
<220> FEATURE:
<223> OTHER INFORMATION: forward primer
```

```
<400> SEQUENCE: 13
agtgaagctt gattttgtag                                        20

<210> SEQ ID NO 14
<211> LENGTH: 20
<212> TYPE: DNA
<213> ORGANISM: Artificial Sequence
<220> FEATURE:
<223> OTHER INFORMATION: foward primer

<400> SEQUENCE: 14
gtgggattaa ttgtgaattt                                        20

<210> SEQ ID NO 15
<211> LENGTH: 18
<212> TYPE: DNA
<213> ORGANISM: Artificial Sequence
<220> FEATURE:
<223> OTHER INFORMATION: reverse primer

<400> SEQUENCE: 15
gaattcacca aaaaaacc                                          18

<210> SEQ ID NO 16
<211> LENGTH: 18
<212> TYPE: DNA
<213> ORGANISM: Artificial Sequence
<220> FEATURE:
<223> OTHER INFORMATION: reverse primer

<400> SEQUENCE: 16
cacactcata tcaatata                                          18

<210> SEQ ID NO 17
<211> LENGTH: 17
<212> TYPE: DNA
<213> ORGANISM: Artificial Sequence
<220> FEATURE:
<223> OTHER INFORMATION: forward primer

<400> SEQUENCE: 17
agtcaagctt ggttgag                                           17

<210> SEQ ID NO 18
<211> LENGTH: 13
<212> TYPE: DNA
<213> ORGANISM: Artificial Sequence
<220> FEATURE:
<223> OTHER INFORMATION: forward primer

<400> SEQUENCE: 18
tgggttgtaa gga                                               13

<210> SEQ ID NO 19
<211> LENGTH: 16
<212> TYPE: DNA
<213> ORGANISM: Artificial Sequence
<220> FEATURE:
<223> OTHER INFORMATION: reverse primer

<400> SEQUENCE: 19
gaattctcca accta                                             16

<210> SEQ ID NO 20
```

```
<211> LENGTH: 13
<212> TYPE: DNA
<213> ORGANISM: Artificial Sequence
<220> FEATURE:
<223> OTHER INFORMATION: reverse primer

<400> SEQUENCE: 20
ctaacccatc acc                                                          13

<210> SEQ ID NO 21
<211> LENGTH: 21
<212> TYPE: DNA
<213> ORGANISM: Artificial Sequence
<220> FEATURE:
<223> OTHER INFORMATION: forward primer

<400> SEQUENCE: 21
agtcaagctt taatgagtgg g                                                 21

<210> SEQ ID NO 22
<211> LENGTH: 20
<212> TYPE: DNA
<213> ORGANISM: Artificial Sequence
<220> FEATURE:
<223> OTHER INFORMATION: forward primer

<400> SEQUENCE: 22
taaaagtaag tattgtatag                                                   20

<210> SEQ ID NO 23
<211> LENGTH: 18
<212> TYPE: DNA
<213> ORGANISM: Artificial Sequence
<220> FEATURE:
<223> OTHER INFORMATION: reverse primer

<400> SEQUENCE: 23
gaattctaat ttaaaacc                                                     18

<210> SEQ ID NO 24
<211> LENGTH: 18
<212> TYPE: DNA
<213> ORGANISM: Artificial Sequence
<220> FEATURE:
<223> OTHER INFORMATION: reverse primer

<400> SEQUENCE: 24
ttaaaactct aacccata                                                     18

<210> SEQ ID NO 25
<211> LENGTH: 20
<212> TYPE: DNA
<213> ORGANISM: Artificial Sequence
<220> FEATURE:
<223> OTHER INFORMATION: forward primer

<400> SEQUENCE: 25
gttttcccag tcacgacgtt                                                   20

<210> SEQ ID NO 26
<211> LENGTH: 20
<212> TYPE: DNA
<213> ORGANISM: Artificial Sequence
<220> FEATURE:
<223> OTHER INFORMATION: reverse primer
```

```
<400> SEQUENCE: 26
tgtggaattg tgagcggata                                              20
```